(12) United States Patent
Childers, Jr. et al.

(10) Patent No.: US 11,844,541 B2
(45) Date of Patent: Dec. 19, 2023

(54) COOLING TOWER

(71) Applicant: Aggreko LLC, New Iberia, LA (US)

(72) Inventors: Billy Wayne Childers, Jr., Chickasha, OK (US); Atul Amar Kumar Swamy, Norman, OK (US)

(73) Assignee: AGGREKO, LLC, New Iberia, LA (US)

( * ) Notice: Subject to any disclaimer, the term of this patent is extended or adjusted under 35 U.S.C. 154(b) by 939 days.

(21) Appl. No.: 16/480,377

(22) PCT Filed: Feb. 2, 2018

(86) PCT No.: PCT/US2018/016637
§ 371 (c)(1),
(2) Date: Jul. 24, 2019

(87) PCT Pub. No.: WO2018/144857
PCT Pub. Date: Aug. 9, 2018

(65) Prior Publication Data
US 2019/0380821 A1 Dec. 19, 2019

Related U.S. Application Data

(60) Provisional application No. 62/454,432, filed on Feb. 3, 2017.

(51) Int. Cl.
*G05D 9/00* (2006.01)
*A61B 17/30* (2006.01)
(Continued)

(52) U.S. Cl.
CPC .............. *A61B 17/30* (2013.01); *A61B 17/29* (2013.01); *A61B 17/3468* (2013.01);
(Continued)

(58) Field of Classification Search
CPC ...... A61B 17/30; A61B 17/29; A61B 17/3468; A61B 17/56; A61B 2017/2937;
(Continued)

(56) References Cited

U.S. PATENT DOCUMENTS 3,784,171 A * 1/1974 Engalitcheff, Jr. ....... F28C 1/02
261/DIG. 11
4,622,183 A * 11/1986 Sonnenschein ......... F28F 25/02
261/DIG. 85
(Continued)

FOREIGN PATENT DOCUMENTS

AU 2008261181 A1 * 7/2009 ............... F28C 1/00
AU 2008261181 A1 7/2009
(Continued)

OTHER PUBLICATIONS

United States Patent and Trademark Office as International Search Authority, International Search Report and Written Opinion for PCT/US2018/016637, dated May 25, 2018, all pages, Alexandria, Virginia, US.

*Primary Examiner* — Claire E Rojohn, III
(74) *Attorney, Agent, or Firm* — LAW OFFICE OF JESSE D. LAMBERT, LLC

(57) ABSTRACT

A cooling tower for evaporative cooling of water is contained within an ISO-compliant shipping container frame, permitting stacking of cooling towers for transport and for certain industrial applications. A volume of fill media is contained within the frame. Spaced apart troughs underlie the fill media, running substantially the length of the fill media and connecting to a basin. Baffles are connected to one upper edge of the troughs, while an air flow space is positioned over the other upper trough edge. A water distribution system, with variable flow nozzles positioned closely above the fill media, sprays water over the upper surface of the fill media, where it moves by gravity down (Continued)

into the troughs. Fans atop the fill media move air vertically upward through the fill media.

13 Claims, 22 Drawing Sheets

(51) Int. Cl.

| | |
|---|---|
| *A61B 17/29* | (2006.01) |
| *A61B 17/34* | (2006.01) |
| *A61B 17/56* | (2006.01) |
| *A61F 2/00* | (2006.01) |
| *F28F 25/04* | (2006.01) |
| *F28C 1/02* | (2006.01) |
| *F28F 25/06* | (2006.01) |

(52) U.S. Cl.
CPC ............ *A61B 17/56* (2013.01); *A61F 2/0063* (2013.01); *F28C 1/02* (2013.01); *F28F 25/04* (2013.01); *F28F 25/06* (2013.01); *A61B 2017/2937* (2013.01); *A61F 2002/0072* (2013.01)

(58) Field of Classification Search
CPC .. A61B 2002/0072; A61F 2/0063; F28C 1/02; F28F 25/04; F28F 25/06

USPC .......................................................... 261/109
See application file for complete search history.

(56) References Cited

U.S. PATENT DOCUMENTS

| | | | | |
|---|---|---|---|---|
| 4,913,710 | A * | 4/1990 | Reverdy | ................... F28C 1/02 55/440 |
| 5,227,095 | A * | 7/1993 | Curtis | ...................... F28C 1/02 261/DIG. 85 |
| 5,317,857 | A | 6/1994 | Allison | |
| 5,487,531 | A | 1/1996 | Curtis | |
| 8,550,274 | B2 | 10/2013 | Gerding | |
| 8,585,024 | B2 * | 11/2013 | Ferree | ..................... F28F 25/04 261/DIG. 11 |
| 11,504,667 | B2 * | 11/2022 | Keith | ..................... B01D 53/18 |
| 2011/0049733 | A1 | 3/2011 | Ferree et al. | |
| 2011/0120592 | A1 | 5/2011 | Gabler | |
| 2019/0063855 | A1 * | 2/2019 | Auth | ..................... F28D 1/0477 |
| 2019/0299122 | A1 * | 10/2019 | Mcdonel | .................. F28C 1/16 |

FOREIGN PATENT DOCUMENTS

| | | |
|---|---|---|
| JP | H06-011296 A | 1/1994 |
| JP | 2005-009750 A | 1/2005 |
| JP | 4638531 B | 12/2010 |

* cited by examiner

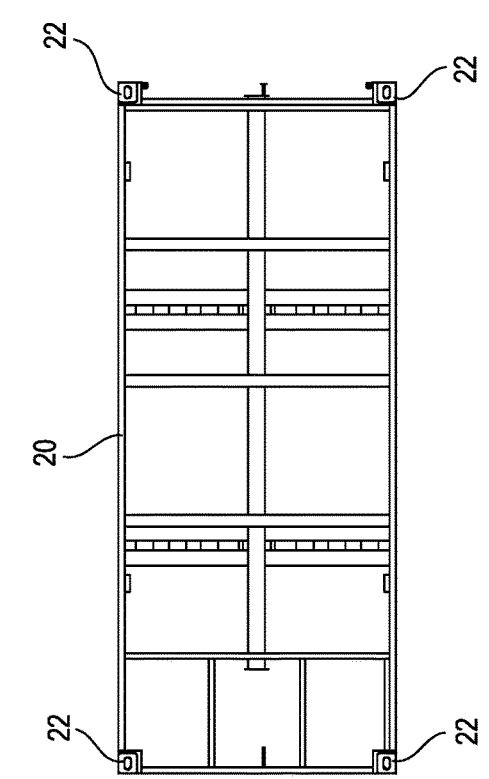
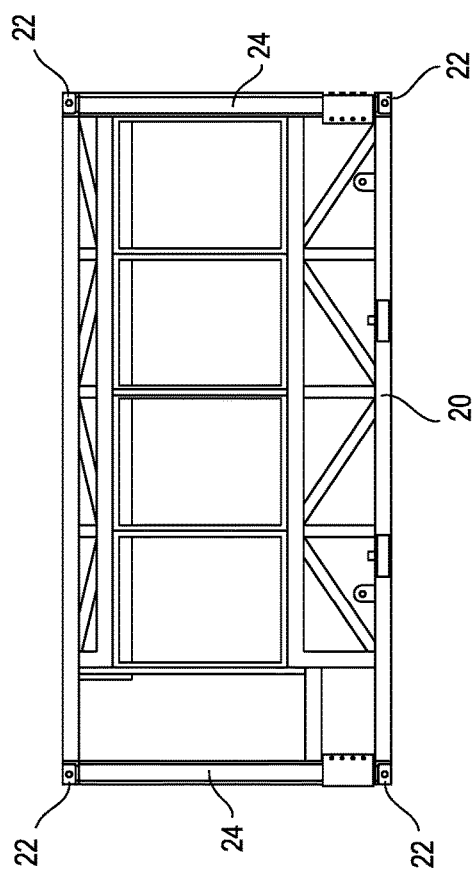
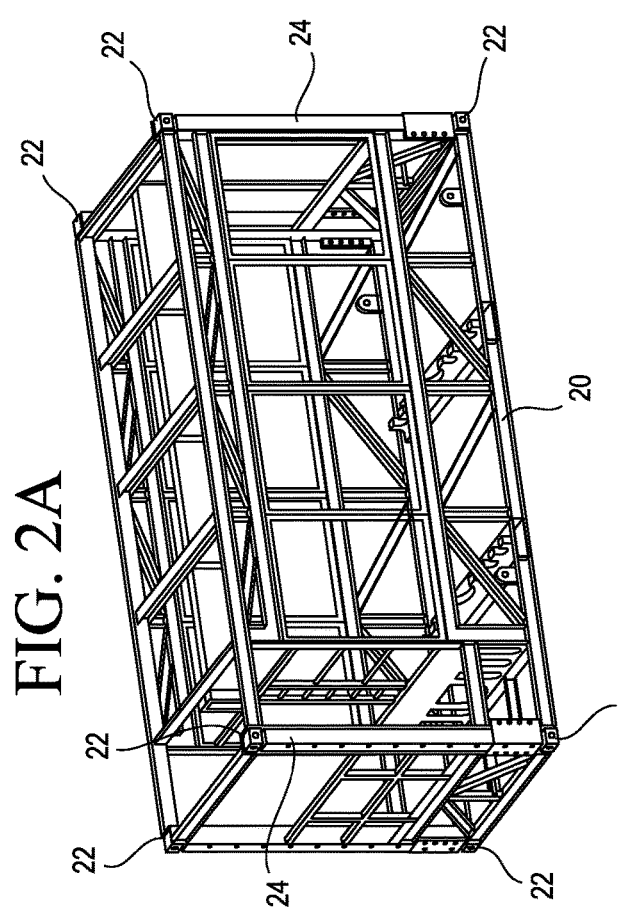
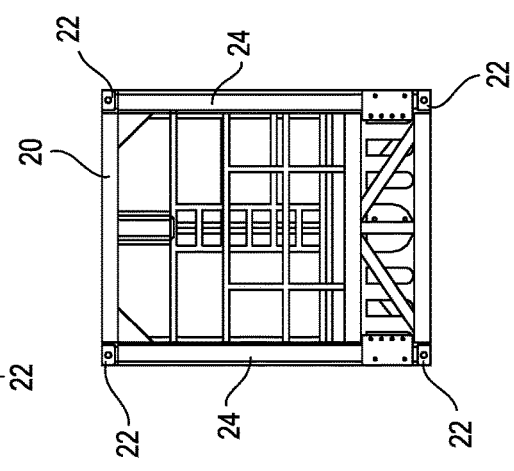

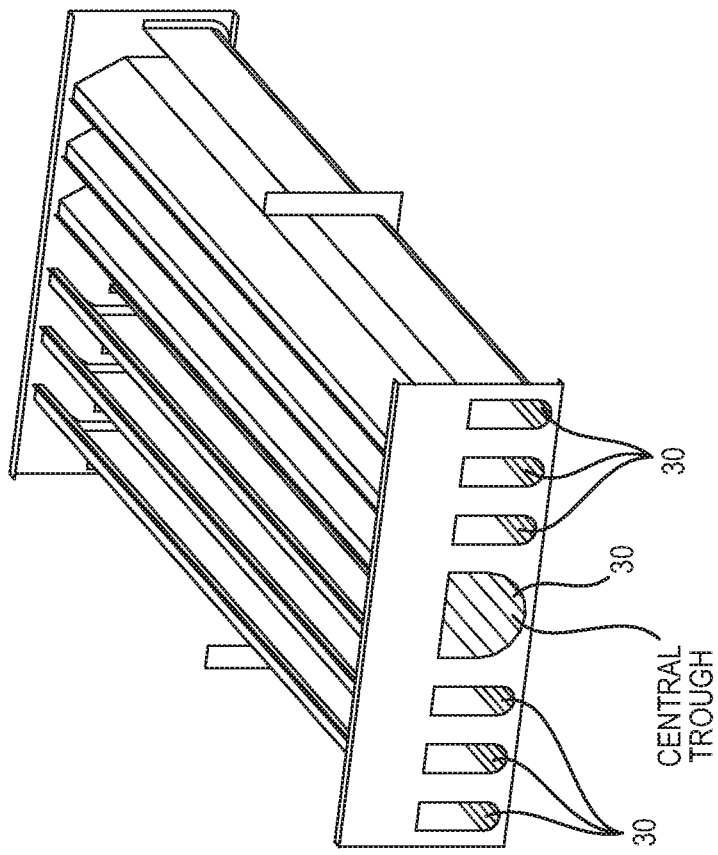
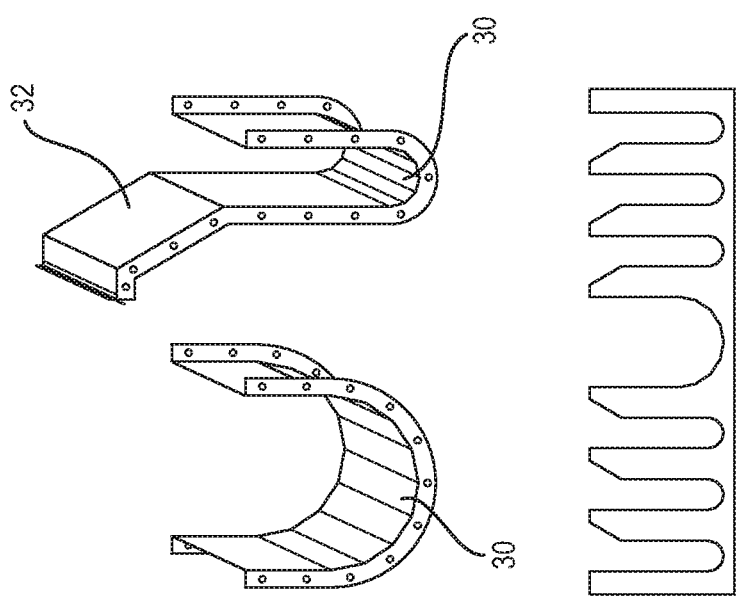
FIG. 9

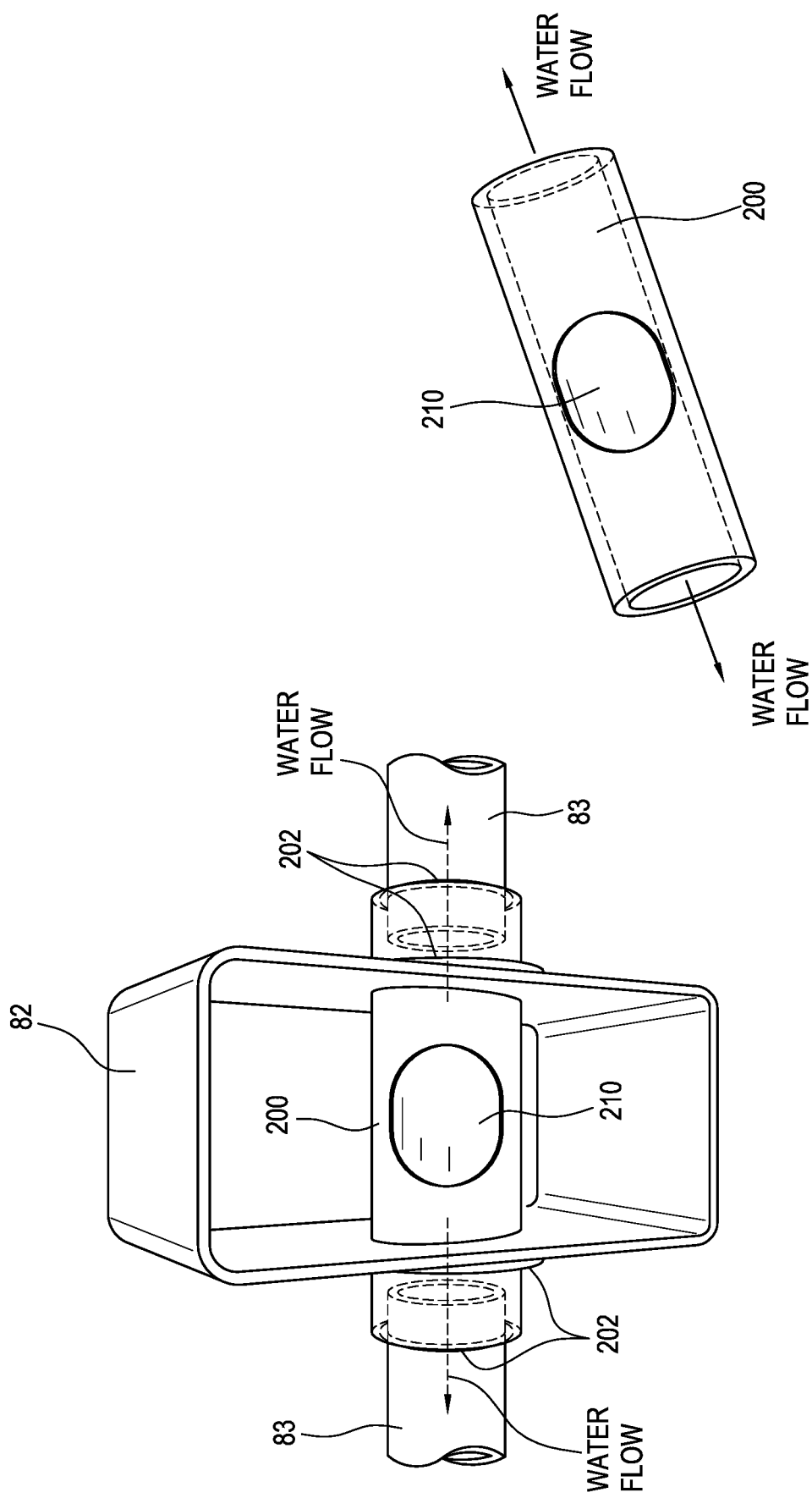

COOLING TOWER

CROSS REFERENCE TO RELATED APPLICATIONS

This non-provisional patent application claims priority to U.S. provisional patent application Ser. 62/454,432, filed Feb. 3, 2017, for all purposes. The disclosure of that provisional patent application is incorporated herein, to the extent not inconsistent with this disclosure.

BACKGROUND

Field of the Invention

This invention relates to cooling towers, typically used for the cooling of liquids, usually water, in industrial and HVAC settings.

Cooling towers, broadly, are heat exchangers that transfer heat from (typically) water sources, referred to herein at times as "hot water." As is known in the relevant art, prior art cooling towers generally share various elements, including a volume of "fill media" within the body of the cooling tower, with some form of water distribution system positioned above the fill media. Water can then be sprayed downwardly onto the fill media, where it moves by gravity through the media to drip out the bottom, and fall into a catch basin. The cooled water is referred to herein at times as "cold water." Air is directed upwardly through the fill media, in "counter flow" to the water moving down, and exits the top of the fill media. Fans positioned above the fill media ("induced draft") or below the fill media ("forced draft") move the air upwardly through the fill media. As is known in the art, the upwardly moving air, in counterflow to the downwardly moving hot water, removes heat from the water.

Known cooling tower designs require a relatively large height dimension, in order to provide vertical spacing for (among other things) sufficient standoff of the water distribution system above the fill media, to permit proper water distribution; and for water to fall from the bottom of the fill media to a catch basin, which generally spans substantially the entirety of the footprint of the cooling tower. In addition, other dimensional and structural attributes prevent placement of cooling towers in desired positions abutting one another, stacked on top of one another, etc. Transportability is yet another issue, with the cooling tower dimensions causing issues with road clearance, etc., frequently requiring disassembly of the portable towers for transport.

The known prior art cooling towers all present these and various other issues, giving rise to a desire for an improved cooling tower that addresses these issues.

SUMMARY OF THE INVENTION

The cooling tower embodying the principles of the present invention comprises an external skeletal frame, which preferably conforms to or can be conforming to Intermodal Freight Container, often referred to as "shipping container," standardized dimensions, thereby being ISO (International Organization for Standardization) compliant; and preferably having ISO (International Organization for Standardization) certified container blocks or corner fittings on the four upper and four lower corners of the frame to connect securing and lifting apparatus. A volume of fill media is positioned in the central part of the overall cooling tower body. A variable flow hot water distribution system comprising a number of low pressure fixed orifice nozzles (with no moving parts), positioned relatively closely above the upper surface of the fill media, sprays the hot water (to-be-cooled) onto the fill media. Preferably, the piping feeding the nozzles (comprising the header and lateral sections) is positioned within a layer of drift eliminator, which captures water mist which is being pulled upwardly by the air stream. The nozzles are therefore positioned between the upper surface of the fill media and the lower surface of the drift eliminator.

A water collection system is positioned below the fill media, to collect the cold water exiting the fill media, and route it as needed to be brought back into the water system. The water collection system comprises a plurality of spaced-apart troughs, which preferably run the length of the cooling tower body or fill media, or in other embodiments span the width of the cooling tower body. Water falls onto baffles positioned above the troughs and which are attached to a first upper edge of the troughs, and angled or slanted so that the water runs into the troughs. From the troughs, the water flows by gravity into a basin or sump at one end of the cooling tower, and from there back into the water system. The present invention may also comprise a water collection system similar to that disclosed in U.S. Pat. No. 8,535,024, owned by the Applicant herein; the disclosure of that patent is incorporated herein to the extent not inconsistent with this disclosure. Air flows upwardly through the spaces between the troughs, and through air flow spaces positioned generally above a second upper edge of the troughs (that is, the upper edge not comprising the baffle). Louvers in the air flow spaces minimize water passage therethrough.

One or more fans are positioned either above (in an "induced draft" system) or below (in a "forced draft" system) the fill media, to move air upwardly through the fill media.

Preferably, telescoping legs are disposed at each corner of the frame. The legs can be extended and locked into position (via pins inserted through holes, or any other suitable means) to elevate the cooling tower as desired for air inlet, and/or to yield sufficient elevation for water drainage into other equipment. The lower end of each leg preferably comprises an ISO compliant corner fitting or corner block. When retracted (and locked into place), the cooling tower transforms into an overall box dimensions that conform to those of a standardized Intermodal Freight Container (an ISO compliant shipping container).

Preferably, external to the main body of the cooling tower but within the skeletal frame is a service access platform. This platform is preferably positioned over the cold water basin (which also extends beyond the main body of the cooling tower but within the skeletal frame), for easy access and service. This section of the overall unit, within the skeletal frame, also comprises inlet and outlet water piping connections, a fan control panel, water fill control, sump screens, access doors, and other components.

BRIEF DESCRIPTION OF THE DRAWINGS

FIGS. 2A-2D are perspective, top, and side views of the skeletal frame of the cooling tower.

FIG. 9 comprises various views of the water collection system troughs, baffles, etc.

FIGS. 20 and 21 show a water flow control arrangement.

DESCRIPTION OF THE PRESENTLY PREFERRED EMBODIMENT(S)

While various cooling towers can embody the principles of the present invention, with reference to the drawings some of the presently preferred embodiments can be described.

Figure 1:
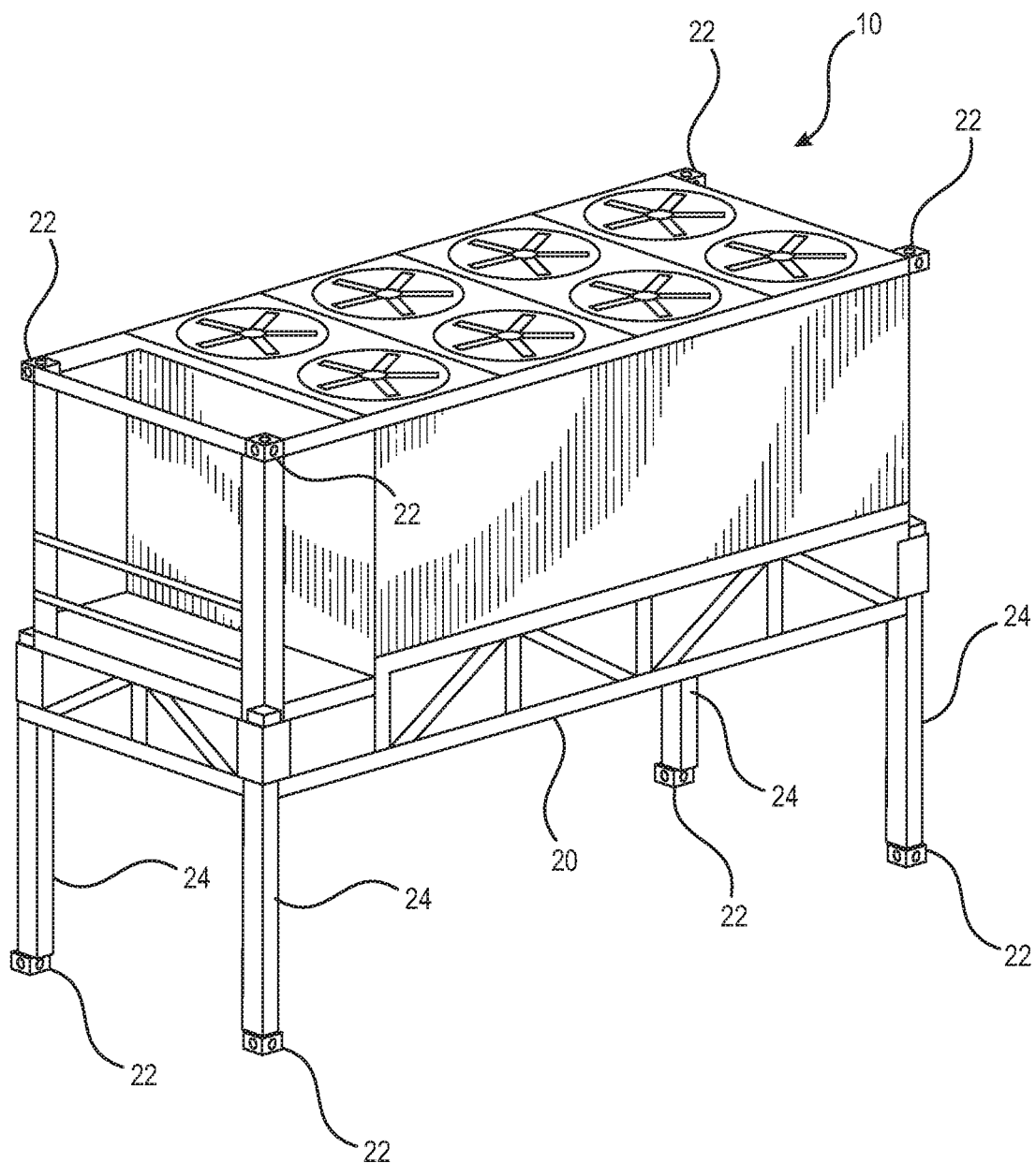
FIG. 1 is a perspective view of an embodiment of a cooling tower embodying the principles of the present invention.

FIG. 1 is a perspective view of one embodiment of the cooling tower 10 embodying the principles of the present invention. Cooling tower 10 comprises a skeletal frame 20, preferably sized to conform to Intermodal Freight Container dimensions, within which is positioned the various elements of the cooling tower. Frame 20 forms an ISO (International Organization for Standardization) compliant structure, and satisfies all structural, material, fabrication and other requirements for such certification. Frame 20 comprises ISO compliant container corner fittings 22 at each corner, for securing and lifting functions. In a presently preferred embodiment, telescoping legs 24 are disposed at the four corners, which can be extended to a desired length and pinned or otherwise secured in place, then retracted when desired for transit, etc. In that embodiment the lower ends of legs 24 also comprise ISO compliant container corner fittings 22. It is understood that the desired elevation of cooling tower 10 above the surface on which it is placed is readily achieved by extending legs 24 a desired distance, then locked in place via pins or other suitable means known in the art. When legs 24 are in their retracted position, the cooling tower is in dimensional compliance with international shipping regulations for Intermodal Freight Containers. It is understood that all other certification requirements for ISO compliance, related to load bearing capability, manufacturing processes and personnel, materials, etc. are satisfied, such that the cooling tower (or the frame thereof) satisfies all ISO compliance requirements. As such, the cooling tower (or the frame thereof) may bear a compliance label.

FIGS. 2A-2D show top, side, and a perspective view of frame 20, legs 24, etc. with legs 24 extended and locked into place at a desired extended length.

Figure 3:
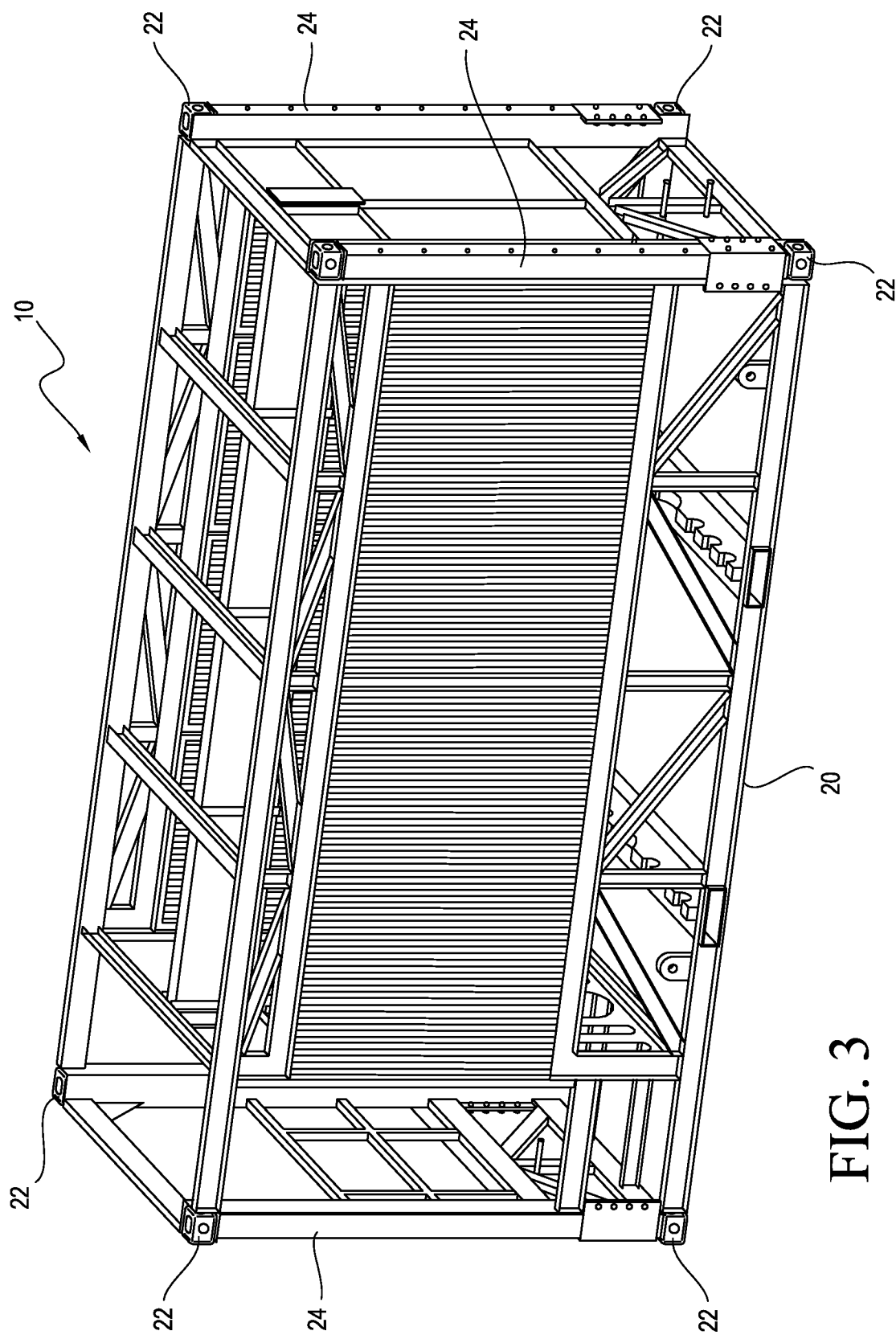
FIG. 3 is a perspective view of the cooling tower skeletal frame, with sheeting in place on the sides.

FIG. 3 is a perspective view of cooling tower 10, particularly frame 20 and legs 24 retracted. Sheet material is also shown in place around the sides of the cooling tower, enclosing the fill media.

Figure 4:
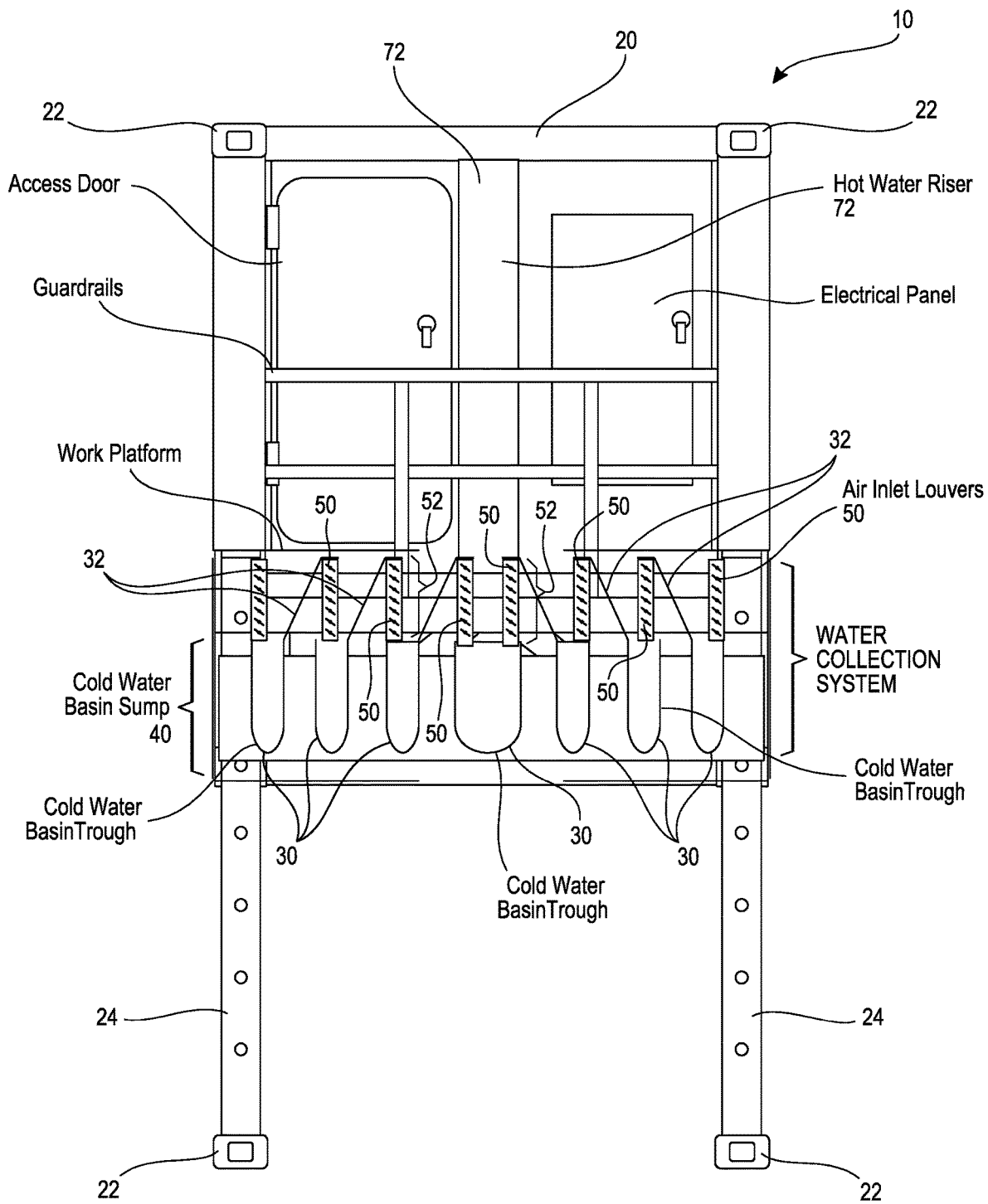
FIG. 4 is an end view of the cooling tower in partial cross section, with the telescoping legs extended.
Figure 5:
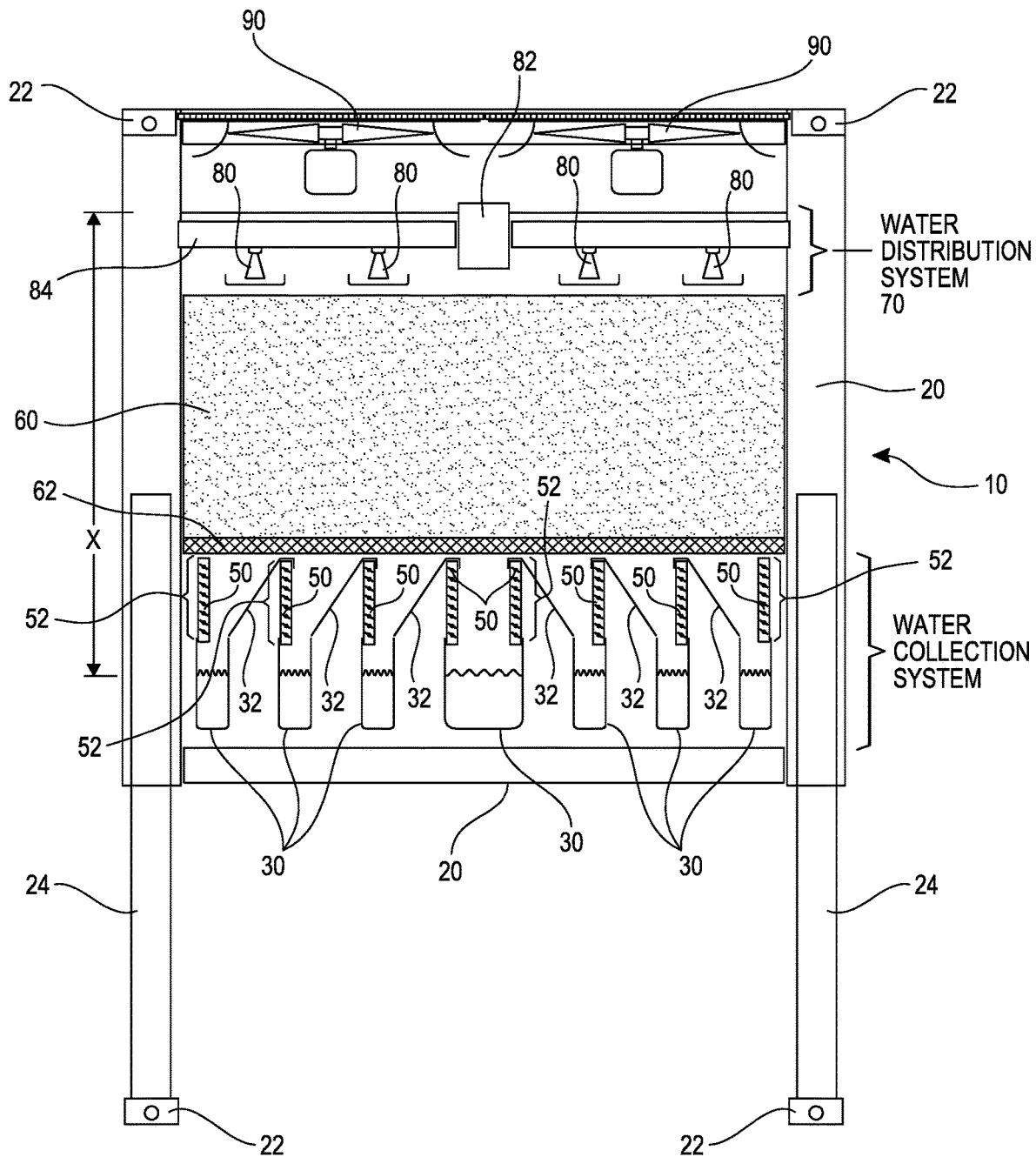
FIG. 5 is another end view of the cooling tower in partial cross section, with the telescoping legs extended.

FIG. 4 is an end view of cooling tower 10, in partial cross section, to show an internal view of a lower section of the cooling tower. In particular, FIG. 4 shows an end view of the troughs 30 (labeled "Cold Water Basin Trough") into which water flows, as it flows out of the fill media 60. Referring to FIGS. 4 and 5, water flows from troughs 30 by gravity into a sump or basin 40 (labeled "Cold Water Basin Sump"), and from there flows to a collection system (comprising piping, pumps, controls, etc.) to be returned to the system from which it came. Troughs 30 comprise first and second upper edges. Baffles 32 are attached to a first of said upper edged and are angled so that water falling downward out of fill media 60 is routed into troughs 30. Air flows into the cooling tower by initially passing between troughs 30, then through air flow spaces 52 above the second trough edge, then upwardly through the fill media 60. Inlet air louvers 50 may be provided to directionally control air flow and prevent water from passing through air flow spaces and thereby not entering troughs 30. Also shown in FIG. 4 are an access door, providing access to internal parts of the cooling tower 10 for maintenance, etc.; the electrical panel door, for service of the various electrical components; and the hot water riser 72, through which hot water (i.e. the water to be cooled by the cooling tower) is pumped up to the water distribution system 70, and on to the fill media 60. A work platform is positioned at one end of cooling tower 10 (note guardrails shown), described in more detail later herein.

Preferably, troughs 30 run lengthwise (e.g. parallel to the long dimension of the cooling tower), substantially the entire length of fill media 60, so that all water drains in a direction parallel to the long dimension of the cooling tower with no cross channels. The cold water can therefore drain in a continuous laminar flow, at a relatively high velocity, preventing areas of very low flow velocity which allows solids deposition. Further, the cold water collection basin 40 preferably lies fully below the cooling tower, preventing the cold water from being exposed to sunlight.

FIG. 5 is an end view in cross section showing various attributes of the cooling tower in more detail. In FIG. 5, legs 24 are extended and pinned or otherwise fixed in place at a desired length from cooling tower 10, so as to elevate cooling tower 10 as desired. Fill media 60 is positioned generally in the central part of cooling tower 10, and may comprise film fill or splash fill materials, as known in the relevant art. In the preferred embodiment, the weight of fill media 60 is supported by internal structural members, e.g. support grating 62, which transfer the weight of fill media 60 to frame 20, rather than supporting the weight of fill media 60 by the water collection system. It is to be understood that in some embodiments, fill media 60 is supported by the water collection system.

A means for distributing water across an upper surface of said fill media is provided, which may comprise water distribution system 70 positioned above fill media 60, and comprises a plurality of spray nozzles 80 through which water to be cooled is sprayed onto fill media 60. The water flows down through fill media 60 by gravity, ultimately exiting fill media 60, dropping onto baffles 32, and then flowing into troughs 30, as briefly described above and described in more detail later herein. FIG. 5 also shows air flow spaces 52 and inlet air louvers 50 positioned above one edge of troughs 30, also to be described in more detail. Spray nozzles 80 are fed by a hot water header 82, which is preferably positioned at least partially within a layer of drift eliminator 84. A plurality of water laterals 81 run from header 82, spray nozzles 80 being mounted on laterals 81. Preferably, spray nozzles 80 of a design with fixed orifices, forming a low pressure, low profile, variable flow system, with no moving parts. Nozzles 80 are preferably mounted only a short distance above the upper surface of fill media 60, for example within a range of about 0.25" to 1.00". It is understood that spray nozzles 80 are positioned within the space between the upper surface of fill media 60 and the lower surface of drift eliminator 84. The design of the cooling tower of the present invention permits a relatively small distance between the upper surface of fill media 60 and the lower surface of drift eliminator 84; in a presently preferred embodiment, this distance is generally about 10" or less, generally within the range of about 8" to 10".

A means for moving air vertically upward through fill media 60 is provided, which may comprise a plurality of fans 90 preferably positioned above water distribution system 70, to pull air through the system in an "induced draft" arrangement, as known in the relevant art. A fan guard/walk grating 92 is positioned above fans 90. It is understood that the present invention also comprises a "forced draft" system, with the fans 90 positioned below the fill media 60, as can be seen in FIG. 8A.

Figure 6:
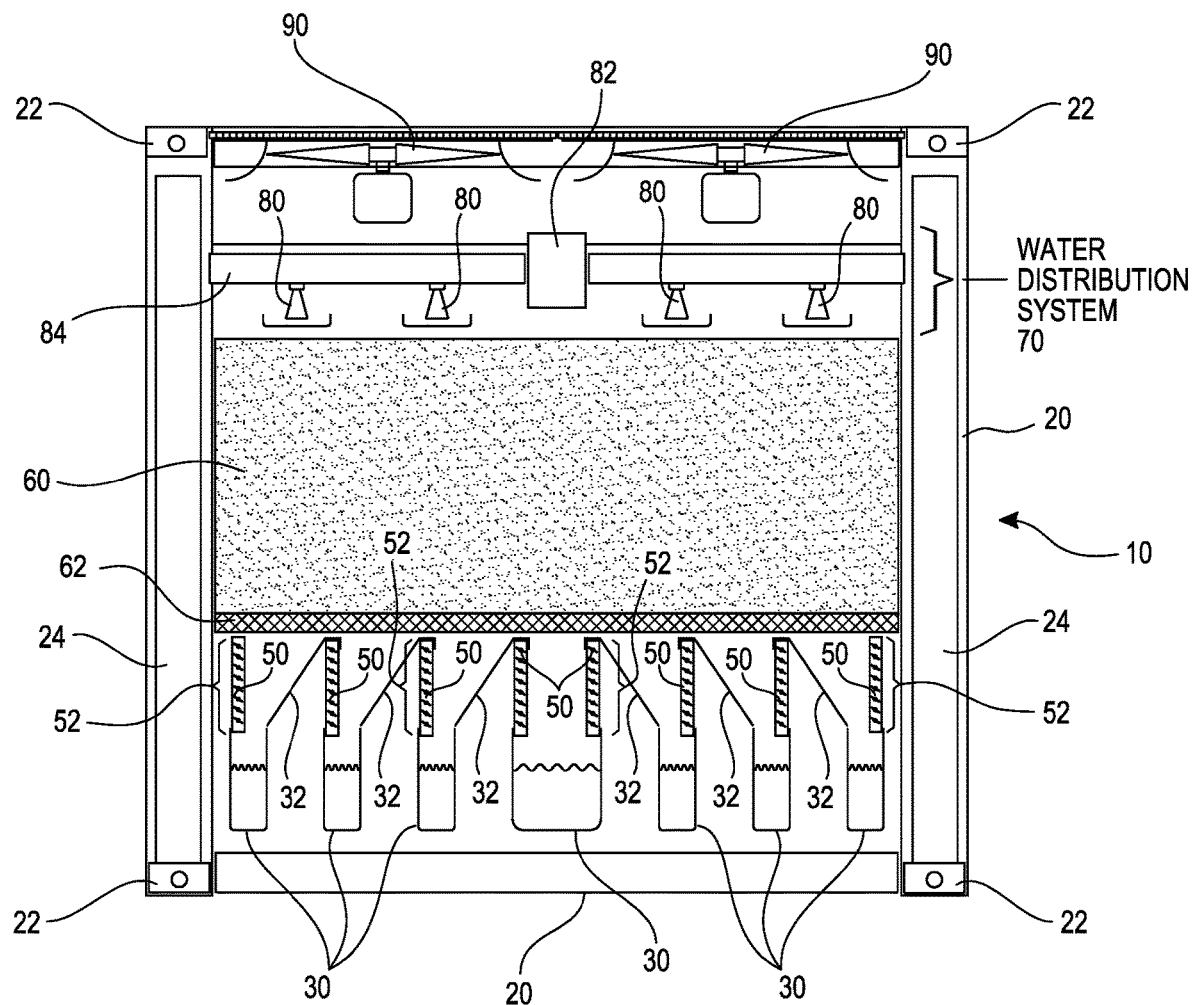
FIG. 6 is another end view of the cooling tower in partial cross section, with the telescoping legs retracted.

As will be understood by those skilled in the relevant art, the cooling tower arrangement embodying the principles of the present invention permits a materially reduced dimension from the level in basin 40 to the water distribution system 70, denoted as dimension "X" in FIG. 5, resulting in a reduced distance that hot water must be pumped vertically up to the hot water distribution system (reduced head value). This results in a decreased pump power requirement, hence lower operating costs (i.e. lower energy costs for hot water pumping). This dimensional aspect is achieved by several structural elements:

- a flow nozzle arrangement permitting a greatly decreased spacing between the upper surface of fill media 60 and the lower surface of drift eliminator 84
- a water collection system comprising the spaced apart troughs, baffles and air flow spaces, eliminating the need for an underlying water sump, instead comprising a basin 40 disposed at the end of the troughs FIG. 6 shows the same view as FIG. 5, but with legs 24 retracted and secured in place, for transit, etc.

Figure 6A:
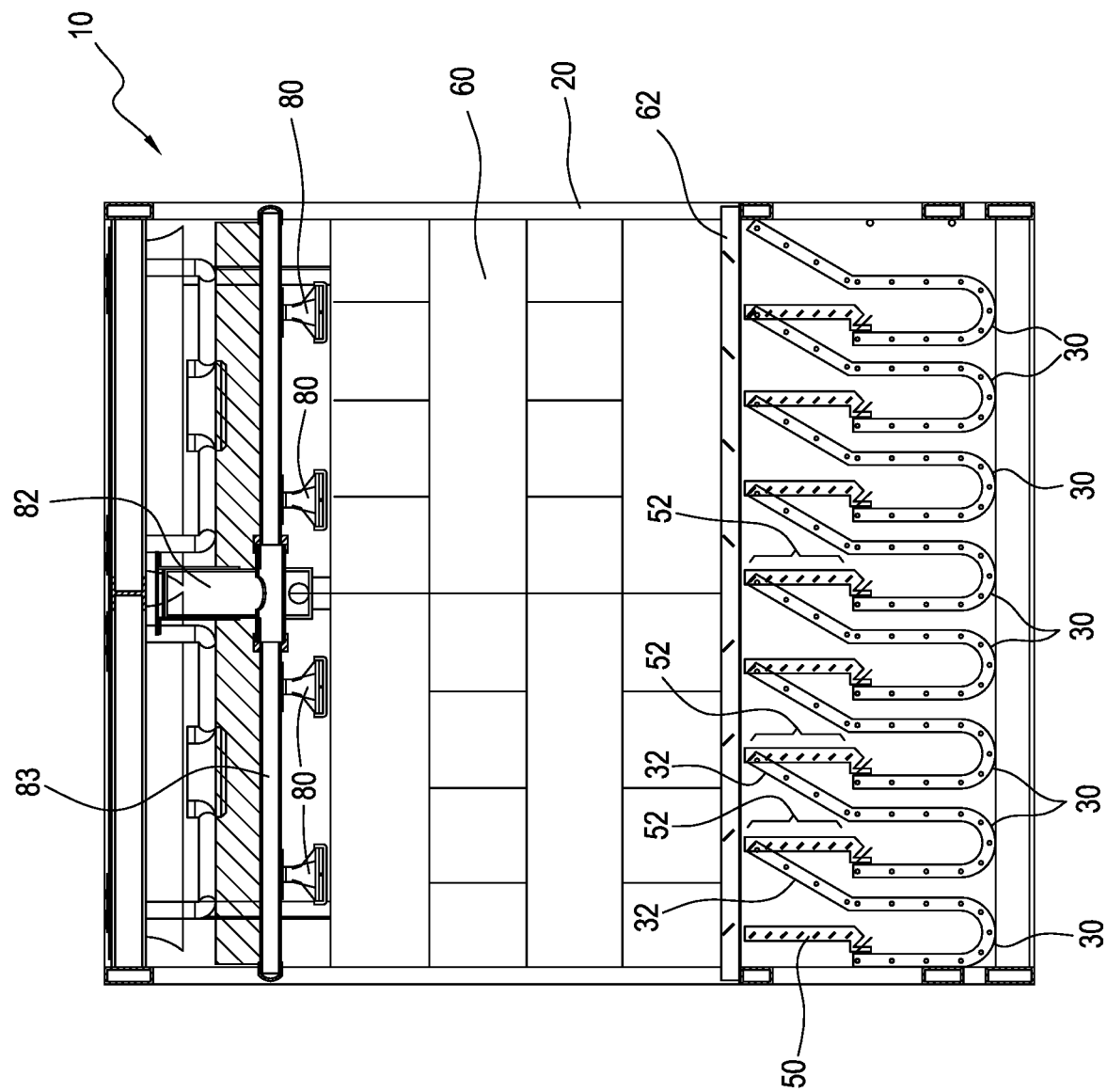
FIG. 6A is a partial cross section showing another arrangement of troughs.

FIG. 6A is a partial cross section of cooling tower 10, showing various elements thereof, with another arrangement of troughs 30.

Figure 7:
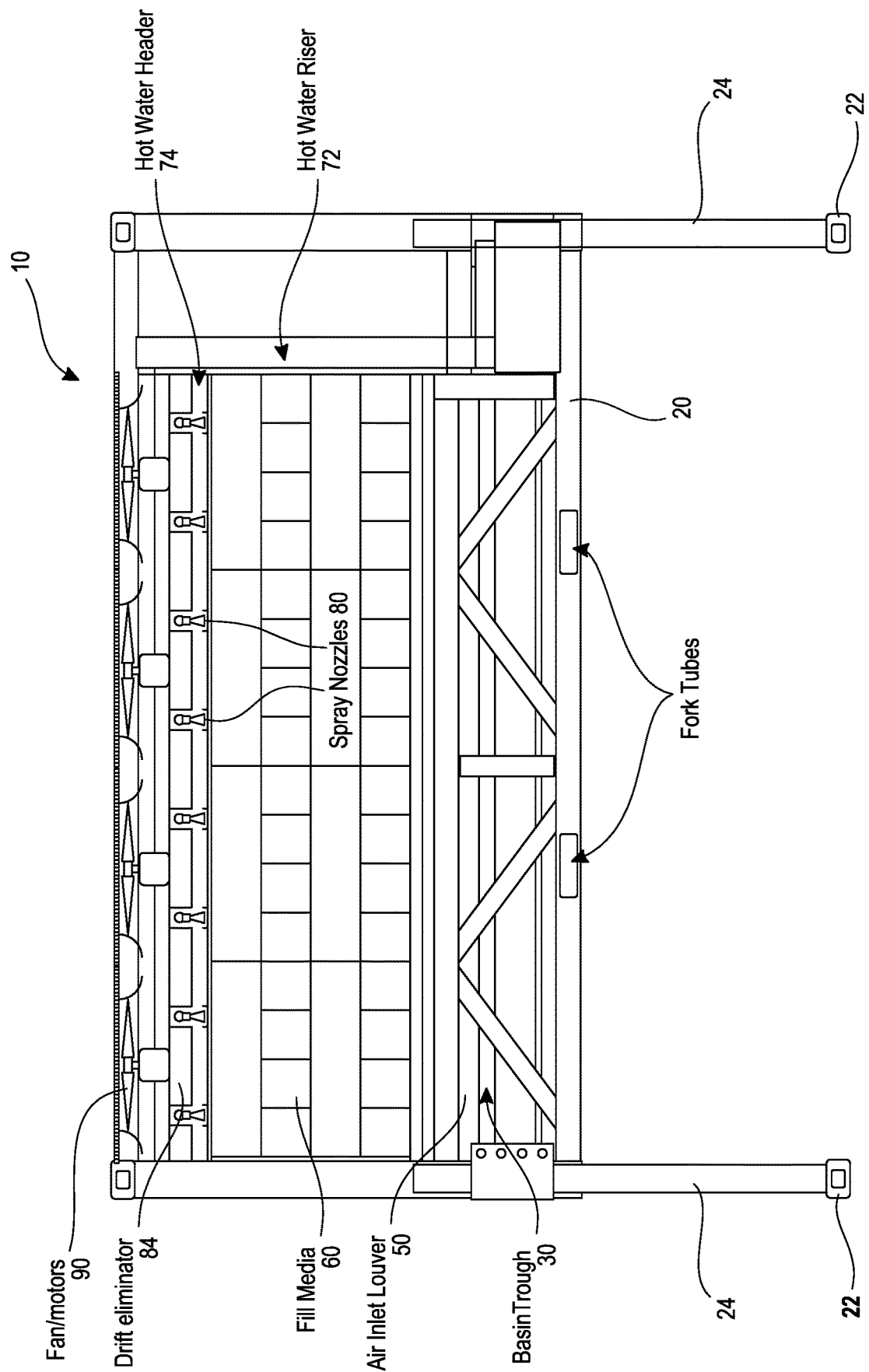
FIG. 7 is a side view of the cooling tower in partial cross section, with the telescoping legs extended.

FIG. 7 is a side view in cross section, showing a number of the same structural elements as seen in FIGS. 5 and 6 and described above. Note that FIG. 7 also shows placement of fork tubes for use by a fork lift or similar apparatus for moving the cooling tower. Hot water riser 72 provides hot water to water distribution system 70, more specifically hot water header 82.

Figure 8:
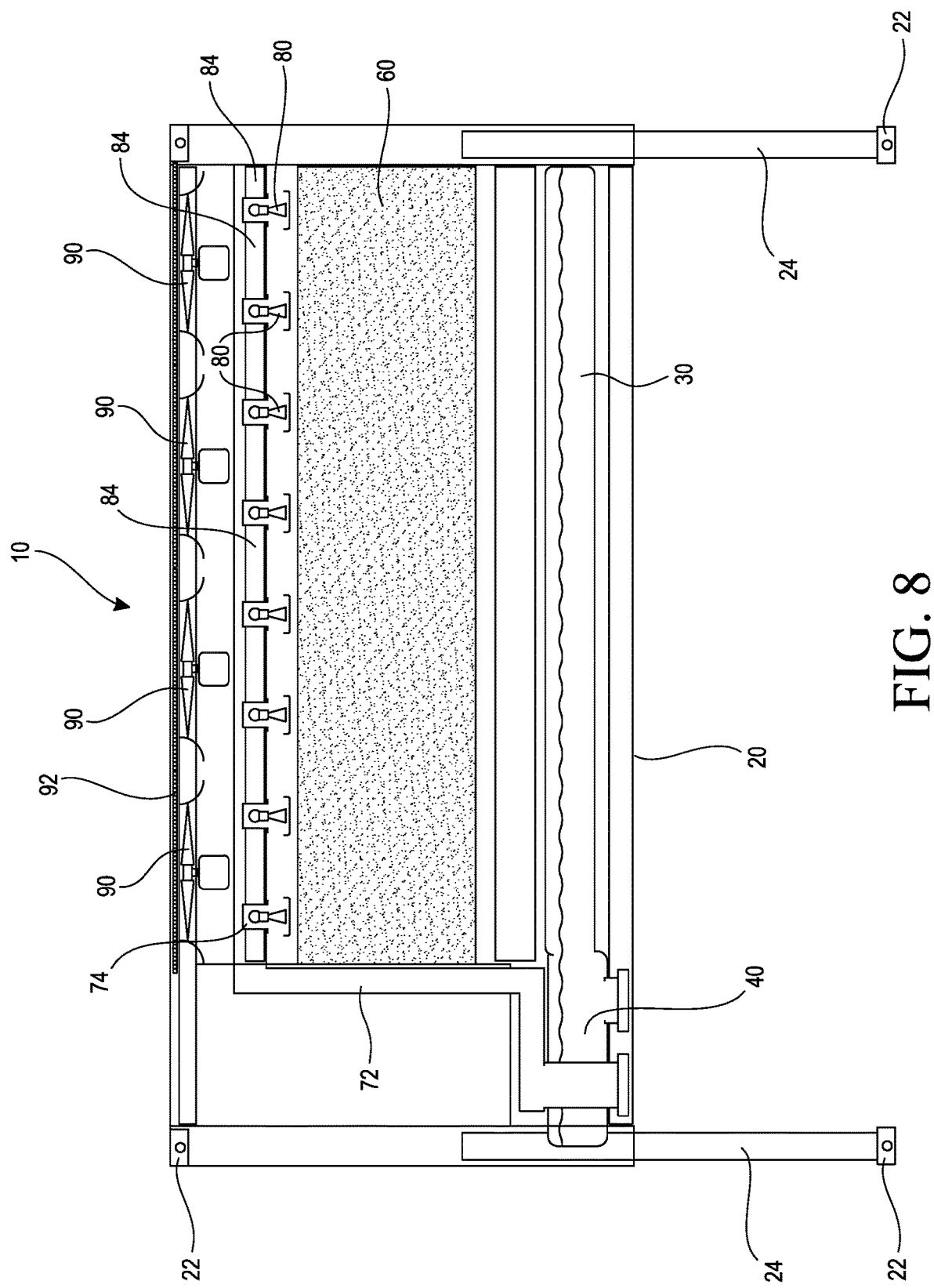
FIG. 8 is another side view of the cooling tower in partial cross section, with the telescoping legs extended, and with certain elements omitted for clarity.
Figure 8A:
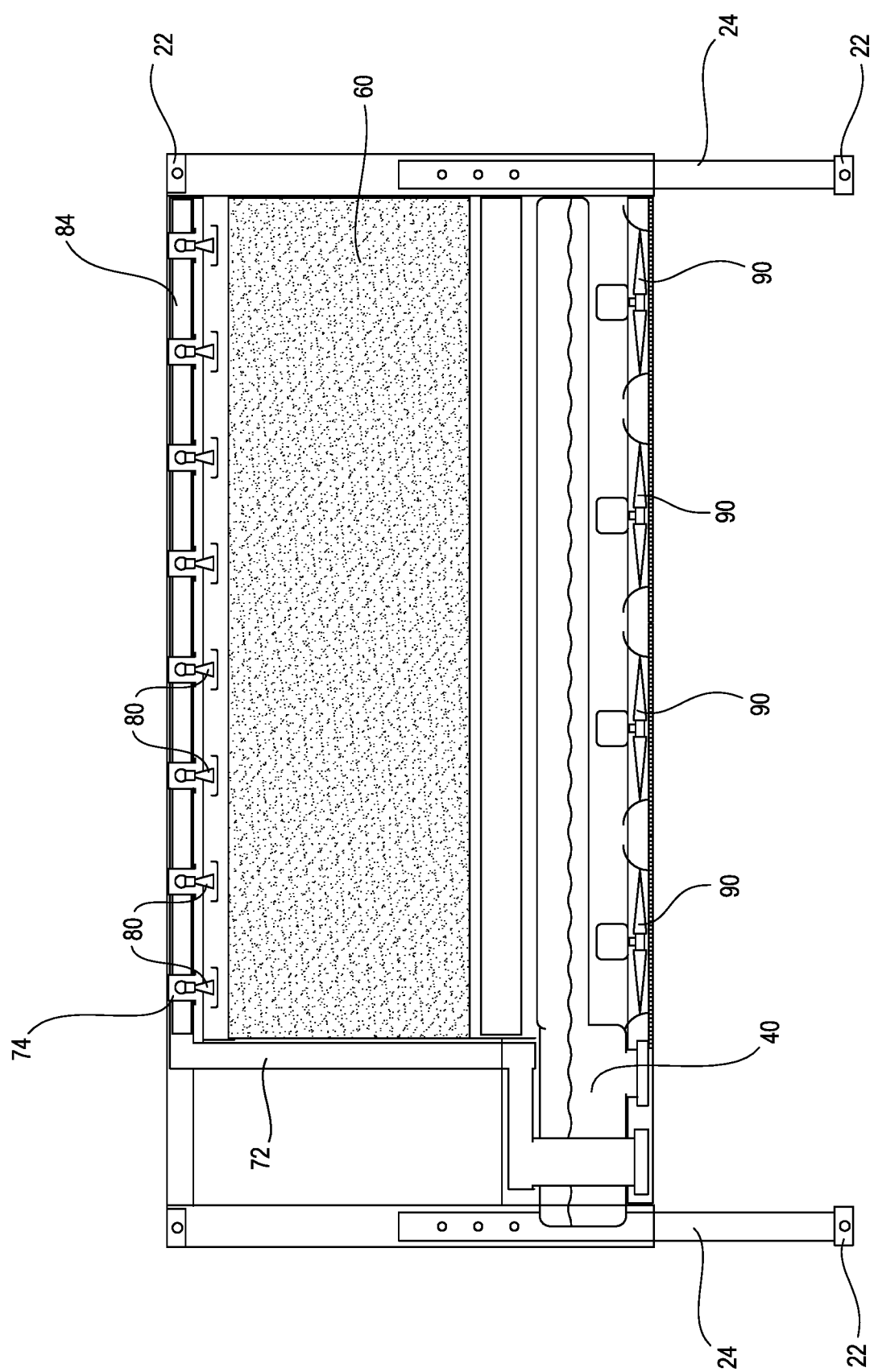
FIG. 8A is a view of a "forced draft" embodiment.

FIG. 8 is another side view in partial cross section. Hot water riser 72, hot water header 82, and cold water basin 40 are clearly seen.

FIG. 8A is a forced draft embodiment, with fans underlying fill media 60.

FIG. 9 comprises several views of troughs 30 and baffles 32, disassembled from the rest of the cooling tower. In one presently preferred embodiment, troughs 30 generally run the length of cooling tower 10; that is, substantially the length of fill media 60. It is to be understood that in other embodiments, troughs 30 can run the width (i.e. the shorter dimension) of cooling tower 10. Note that baffles 32 are not required to route water into the central trough (labeled), due to the arrangement of other elements of the system.

Figure 10:
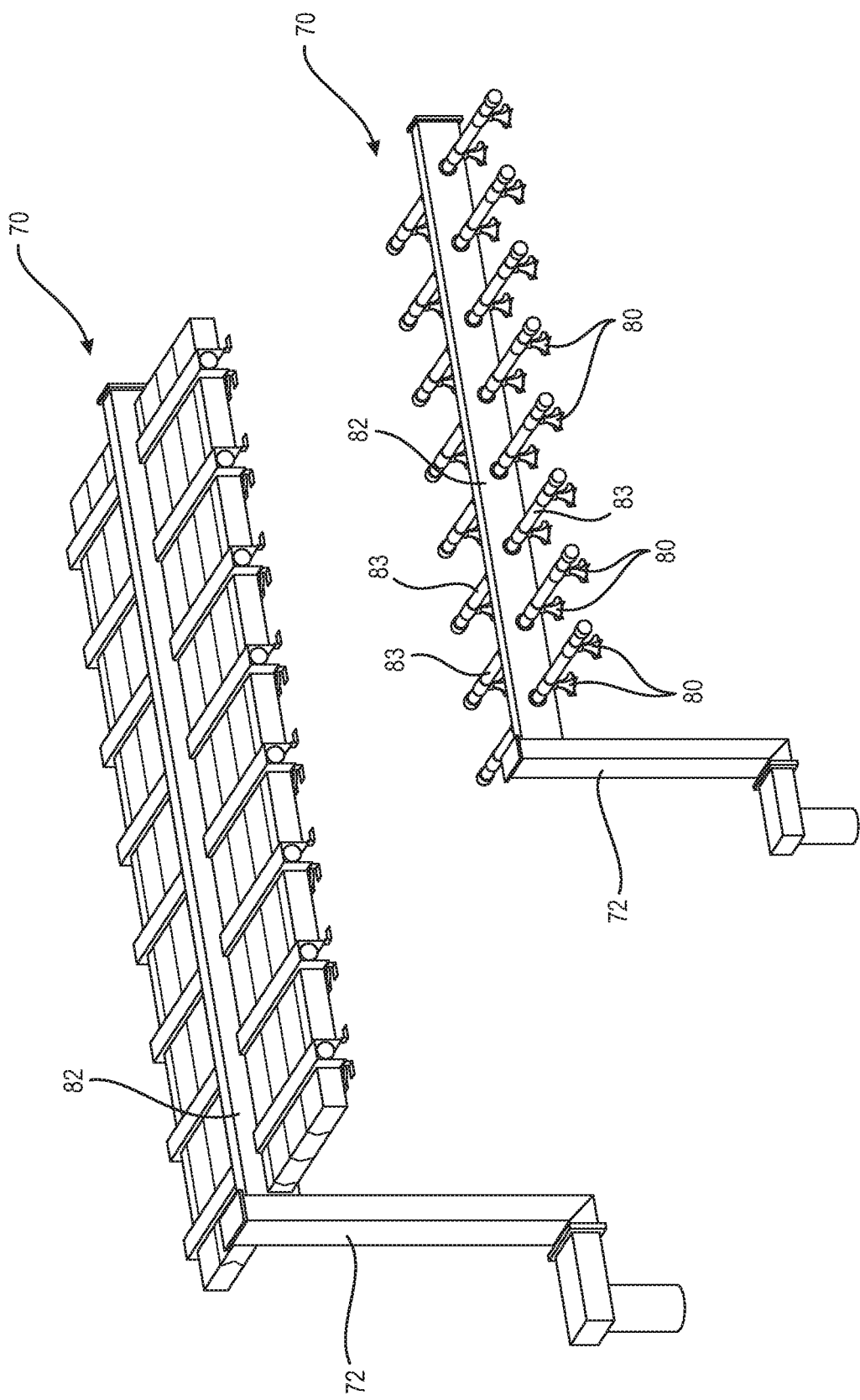
FIG. 10 is a perspective view of the water distribution system.

FIG. 10 is a detailed view of water distribution system 70 separated from the other components. Water is pumped from the hot water source to the hot water riser(s) 72, into hot water header 82, through laterals 83 then to spray nozzles 80 and out onto the upper surface of fill media 60. Drift eliminator 84 is shown, which reduces the amount of water droplets which are carried out of the cooling tower by the upward air flow.

Figure 11:
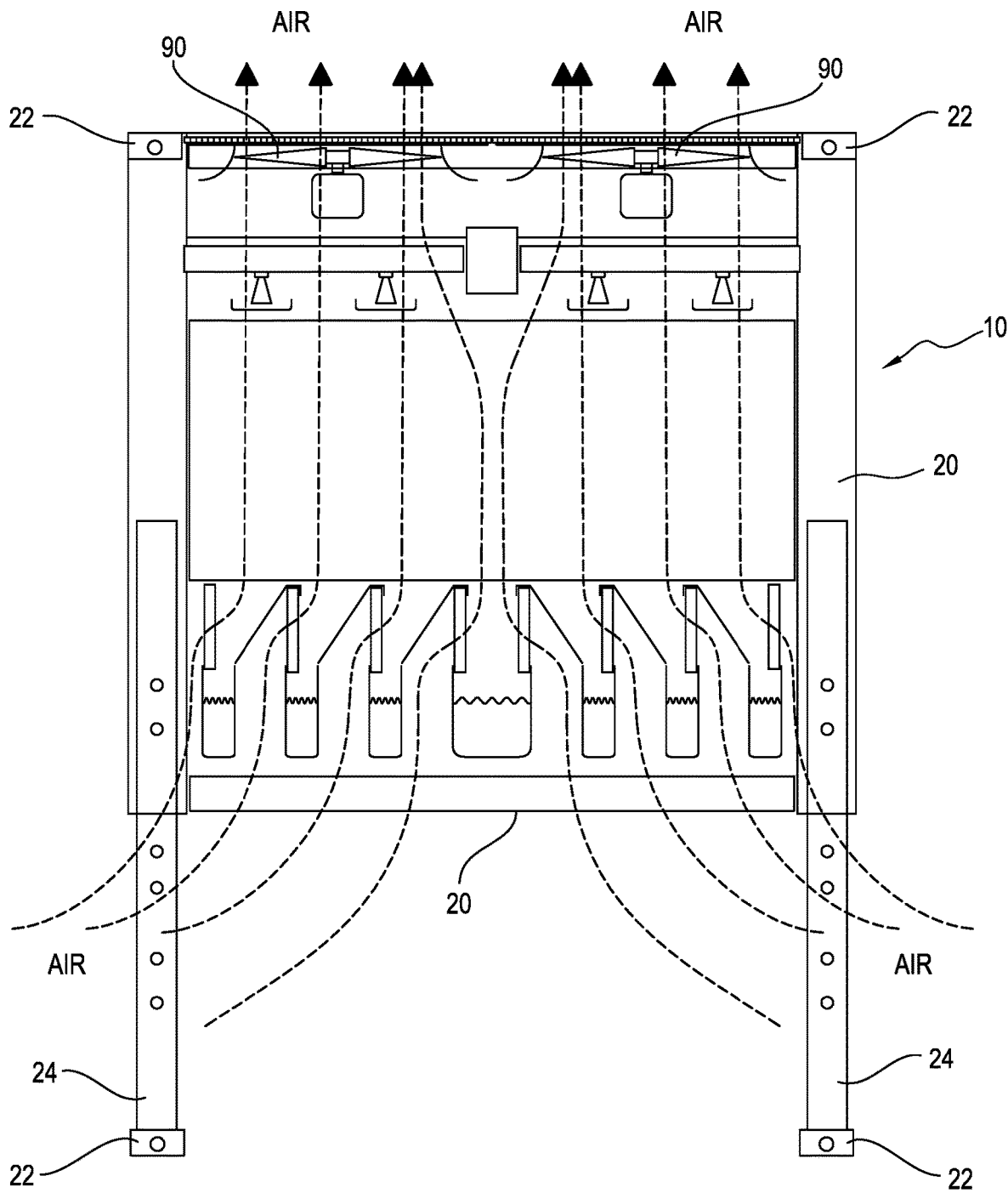
FIG. 11 is an end view in partial cross section, illustrating the air flow path through the cooling tower.

FIG. 11 shows typical air flow paths through cooling tower 10, as the air is being "pulled" through the system by fans 90, in an "induced draft" arrangement. Note that certain element numbers are omitted for clarity. Air generally enters from the bottom of cooling tower 10, flowing vertically upward between troughs 30, through air flow spaces 52 and inlet air louvers 50, and then upwardly through fill media 60. Air exits fill media 60, flowing upwardly through drift eliminator 84, through fans 90 and fan guard/walk grating 92, then exiting cooling tower 10. It is understood that the arrangement shown in FIG. 11, and the other figures, is only one possible arrangement; a "forced draft" arrangement is also possible, having fans positioned below the troughs and other components, and thereby "pushing" air through the fill media and other components of the system; reference is again made to FIG. 8A.

Figure 12:
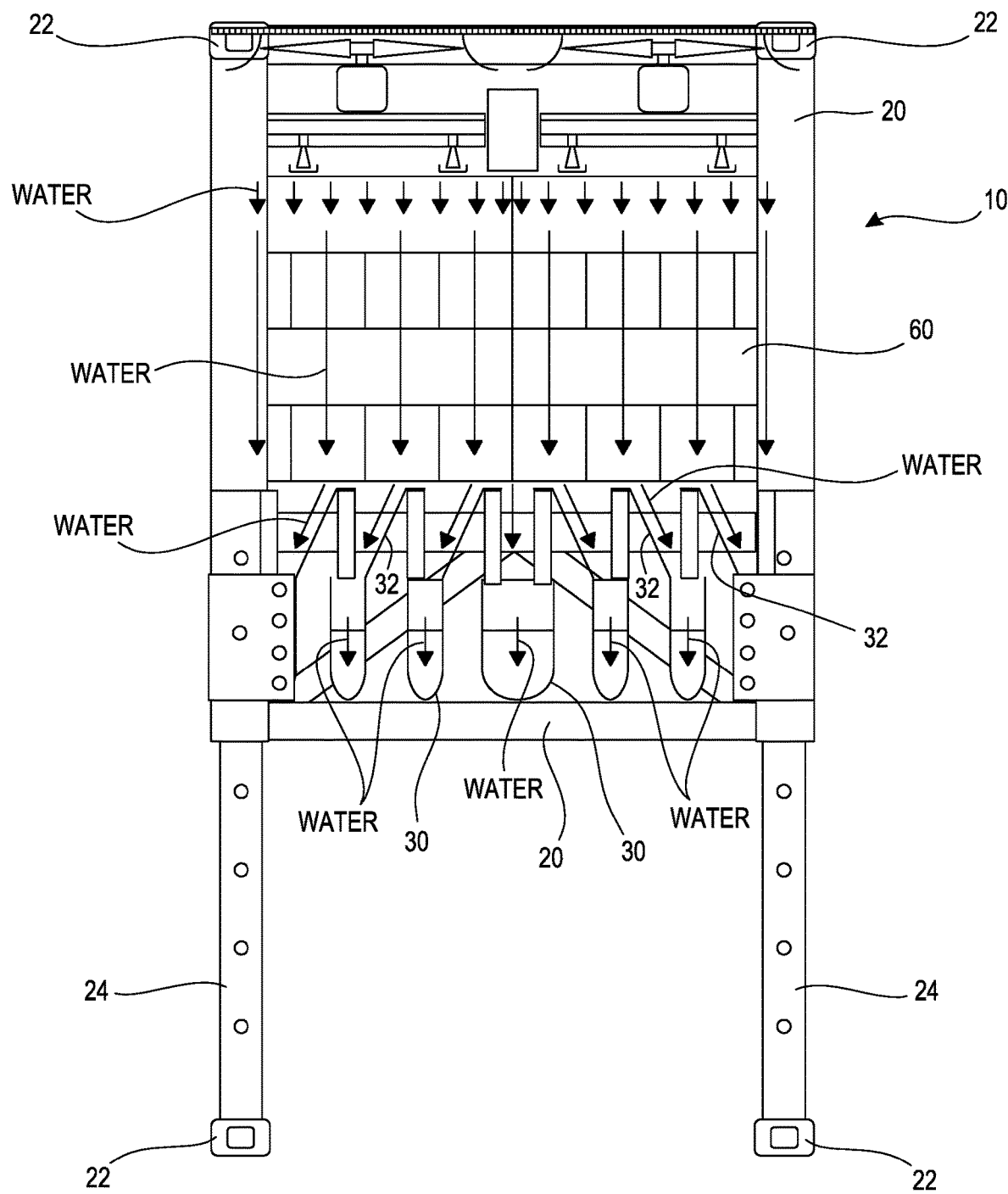
FIG. 12 is an end view in partial cross section, illustrating the water flow path through the cooling tower.
Figure 13B:
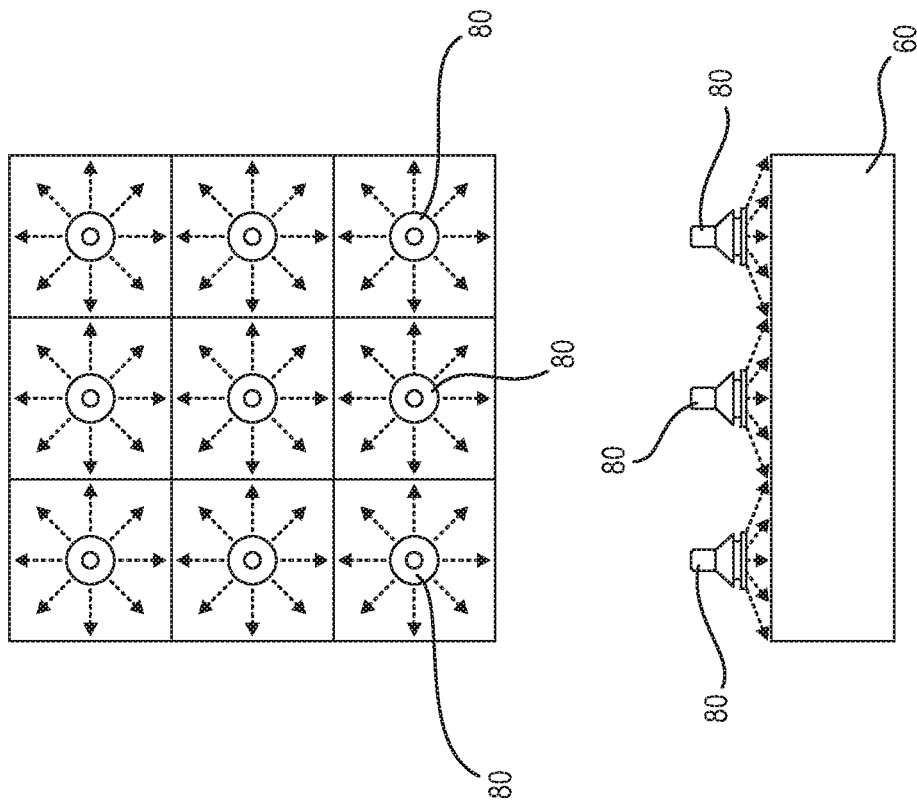
FIG. 13B illustrates an exemplary water nozzle arrangement embodying the principles of the present invention.
Figure 13A:
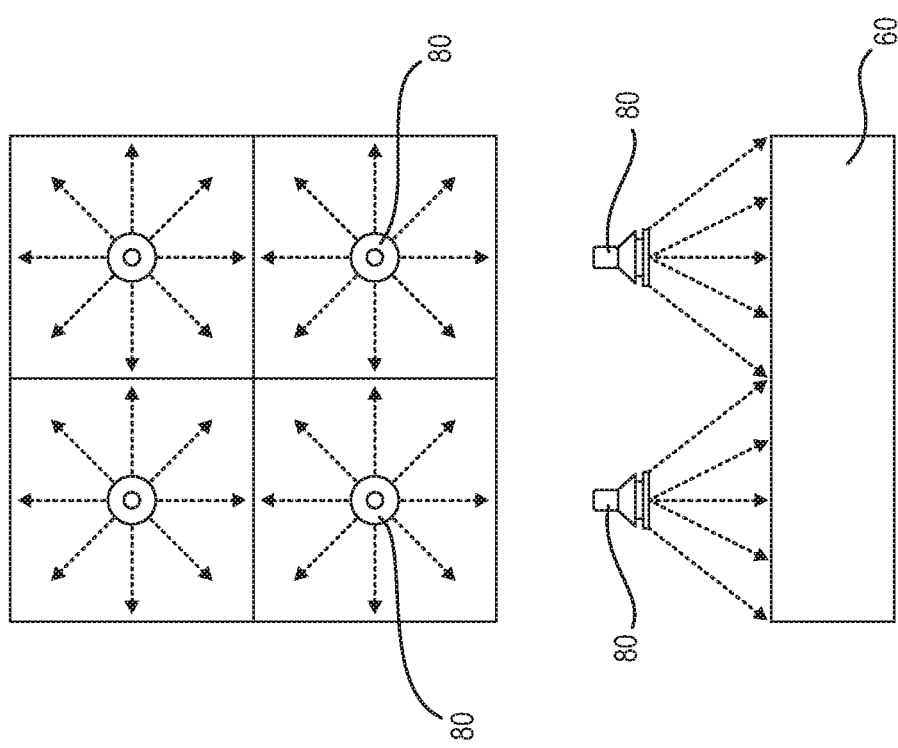
FIG. 13A illustrates a prior art water nozzle arrangement.

FIG. 12 shows typical water flow paths through the system. Certain element numbers are omitted for clarity. Hot water exits flow nozzles 80 onto the upper most surface of fill media 60. The water flows by gravity through fill media 60, exiting the fill media 60 as "cold water" and ultimately flowing into troughs 30, either by flowing onto baffles 32 and then into troughs 30, or directly into troughs 30. The cold water flows by gravity into a basin 40 (see FIG. 8), then to a system (typically comprising pumps, piping, etc.) to return it to a system to be cooled, e.g. a heating/ventilation/air conditioning (HVAC) system, an internal combustion engine cooling system, or any other system as known in the relevant art. As noted above, the present invention may also comprise a water collection system similar to that disclosed in U.S. Pat. No. 8,535,024, owned by the Applicant herein; the disclosure of that patent is incorporated herein to the extent not inconsistent with this disclosure FIGS. 13A and 13B show flow nozzle arrangement per the prior art (13A) and the present invention (13B). As can be seen in FIG. 13A, prior art systems generally used fewer nozzles per unit area, typically requiring a higher standoff (i.e. distance from the nozzle to the fill media surface) to provide the desired coverage. By way of example, known prior art systems may employ four nozzles in a 6' by 6' area (i.e. 4 nozzles in 36 square feet). In contrast, a flow nozzle arrangement embodying the principles of the present invention, as seen in FIG. 13B, comprises a greater number of nozzles per unit area, namely multiple low pressure nozzles, that spray/disperse the water more horizontally. By way of example, a preferred arrangement of the present invention may comprise five nozzles in a 4'×4' area (i.e. 5 nozzles in 16 square feet). These features of the present system permit a lower standoff of the flow nozzles above the fill media, hence the use of less vertical space than prior art systems, namely, a greatly reduced distance from the upper surface of fill media 60 to the flow nozzle 80 discharge, and consequently to the lower surface of drift eliminator 84. Additionally, the greater number of nozzles per unit area achieves better coverage of the fill media when pressure/flows are varied.

Figure 14:
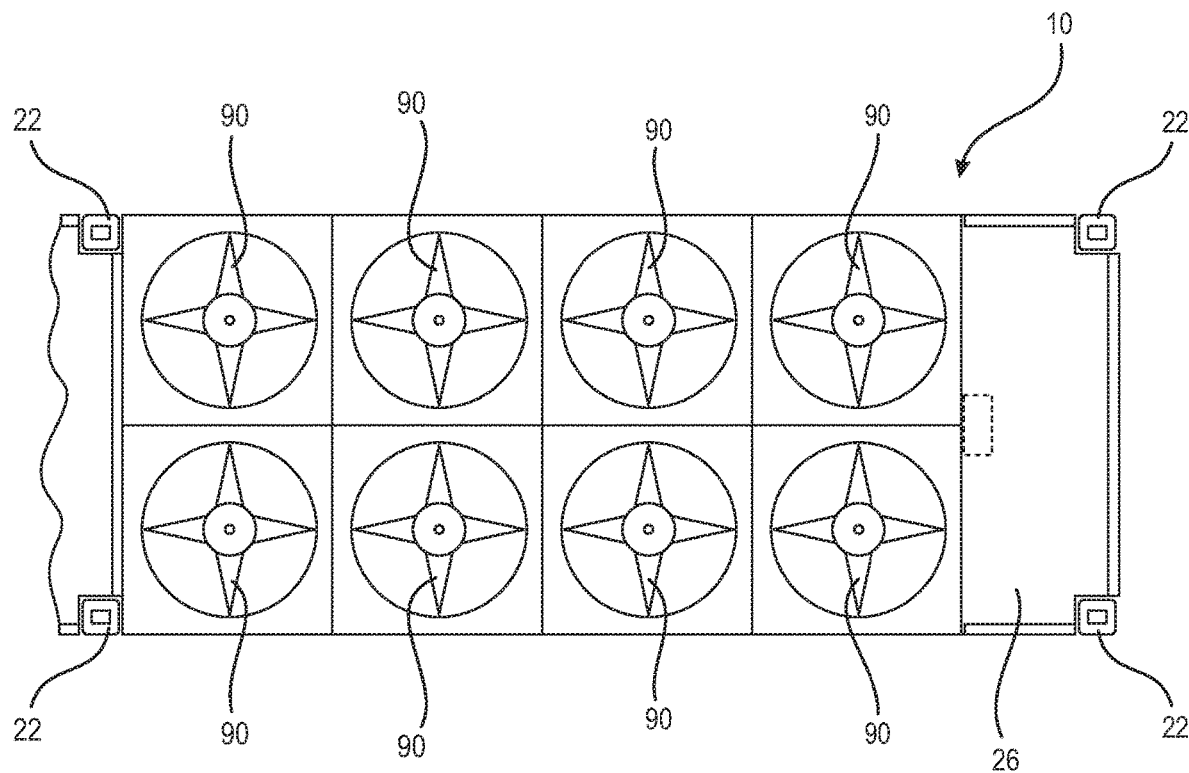
FIG. 14 is a top view of a single cooling tower.

FIG. 14 is a top view of cooling tower 10. Work platform 26 is seen at one end of cooling tower 10, outside of the fill media 60 area but within frame 20. Preferably, basin 40 underlies work platform 26, permitting easy access for service, etc. In addition, positioning basin 40 beneath work platform 26 and/or other structural elements of cooling tower 10 shields water within basin 40 from sunlight, thereby avoiding temperature increases due to sun exposure.

Figure 15:
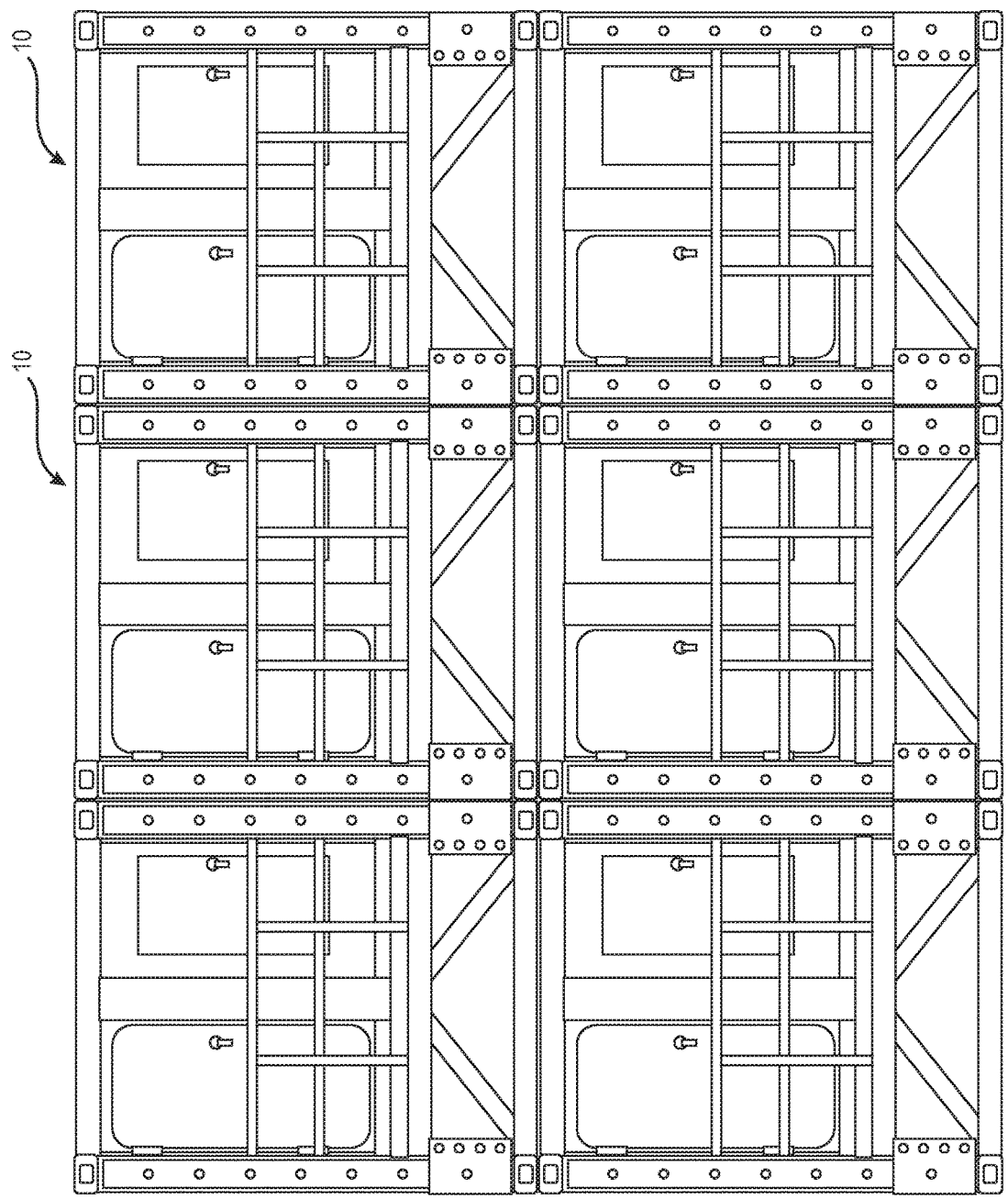
FIG. 15 is an end view of a number of cooling towers, with the telescoping legs retracted, showing the towers stacked, e.g. for bulk transit or storage.

FIG. 15 shows a number of cooling towers 10 with legs 24 retracted and stacked for transit. It can be readily appreciated that with the dimensions of frame 20 conforming to standard Intermodal Freight Container dimensions, cooling towers 10 may be readily handled and shipped, and stacked for bulk transit and storage. As known in the relevant art, corner fittings 22 permit cooling towers 10 to be connected one to another. As with the remaining elements of frame 20, corner fittings 22 are ISO compliant container corner fittings, meeting ISO requirements for shipping containers.

Figure 16:
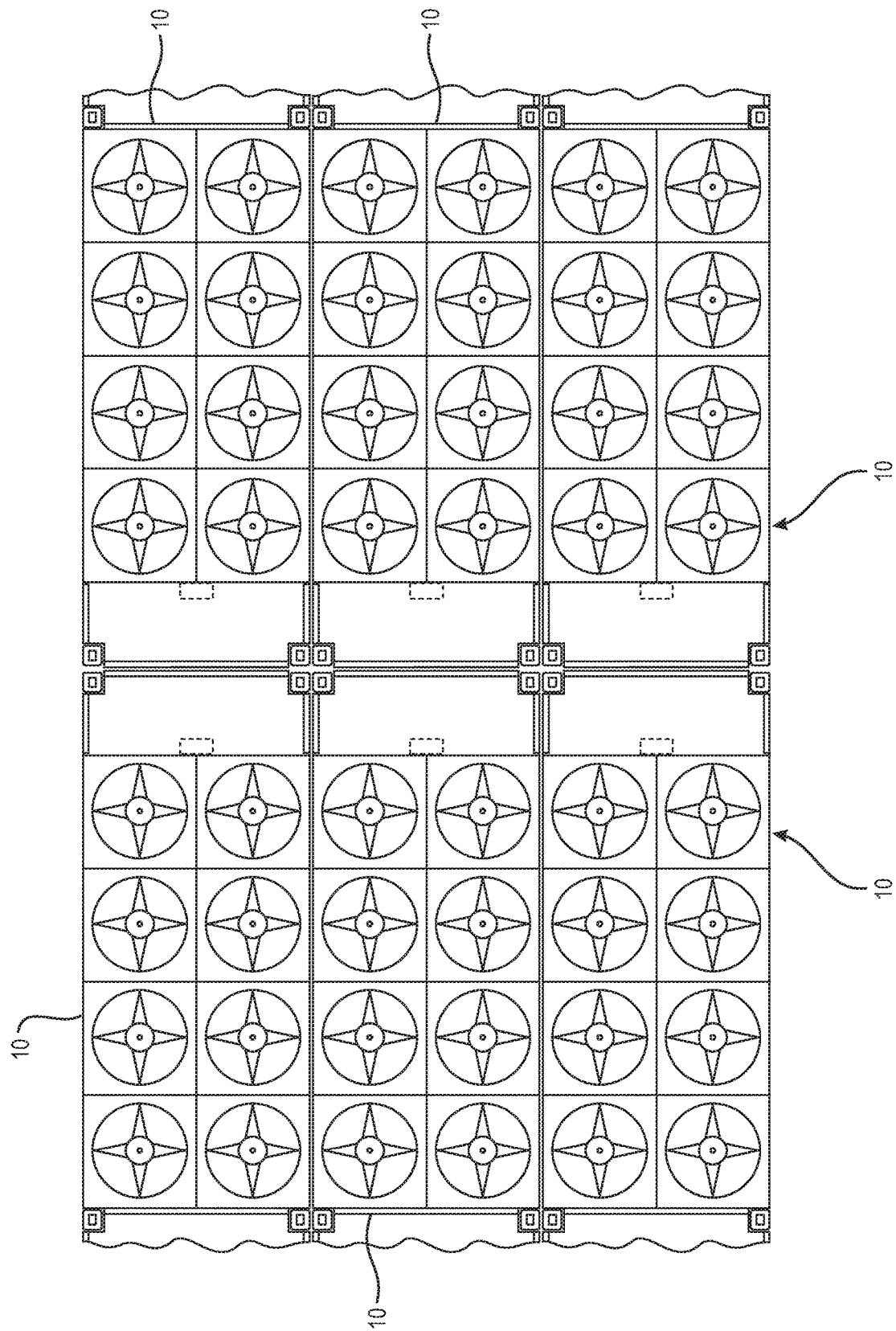
FIG. 16 is a top view of one arrangement of multiple cooling towers positioned adjacent one another.
Figure 17:
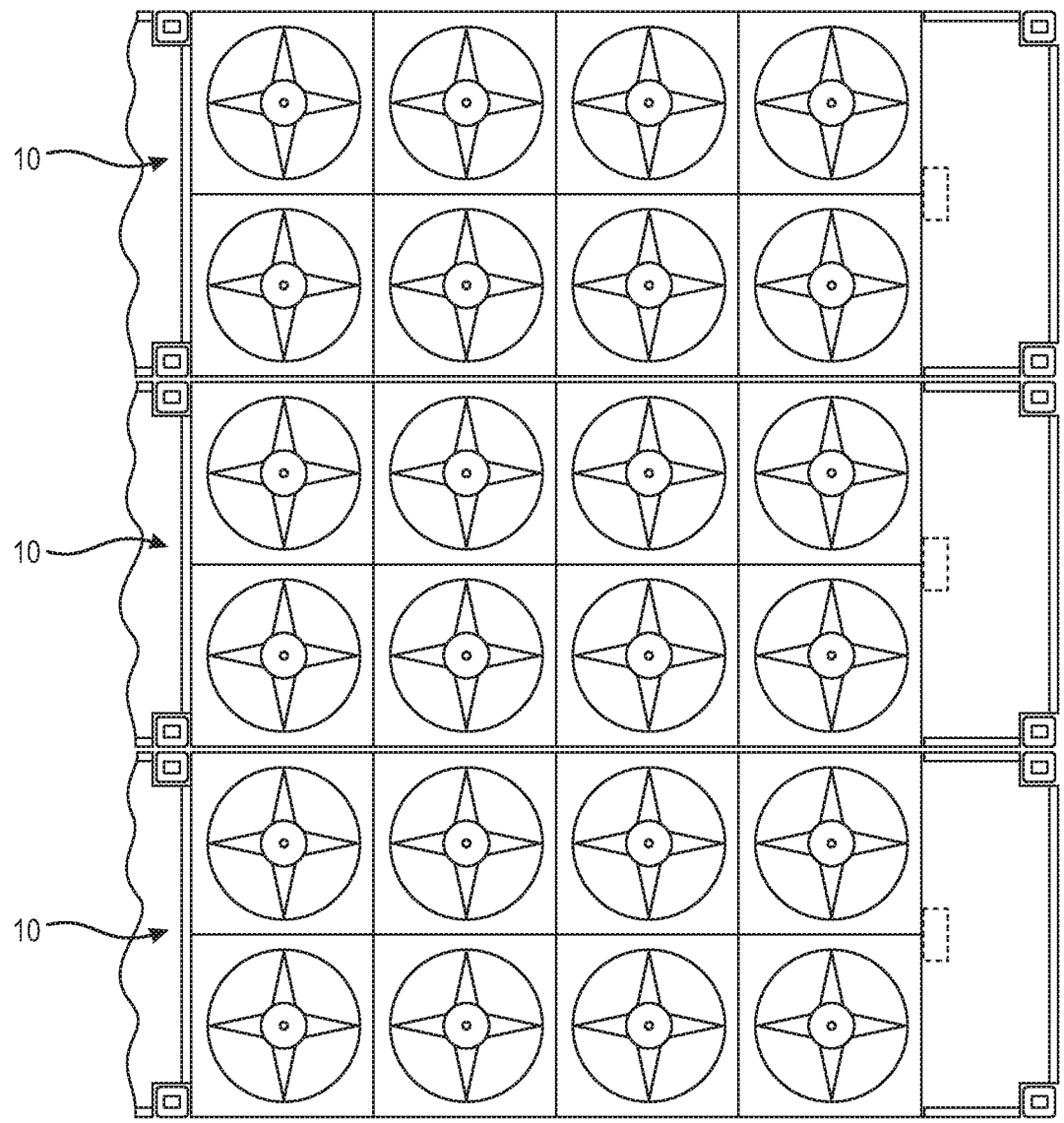
FIG. 17 is a top view of another arrangement of multiple cooling towers positioned adjacent one another.

As previously described, air enters cooling tower 10 from the bottom, rather than from the sides, hence cooling towers 10 of the present invention may be positioned adjacent to, and abutting, one another, without loss of effectiveness. There is no need to position the cooling towers 10 spaced apart from one another, to permit air flow. Such placement permits greatly increased cooling tower "density," i.e. cooling capacity per unit of ground area. Various placement configurations are possible. One configuration is shown in FIG. 16, with two sets of three cooling towers 10 abutting one another, with the work platform ends together. FIG. 17 shows an alternative arrangement of cooling tower 10 placement. It is to be understood that any arrangement of the cooling towers 10 is possible; e.g. either end of a given cooling tower abutting either end of another cooling tower 10.

Figure 18:
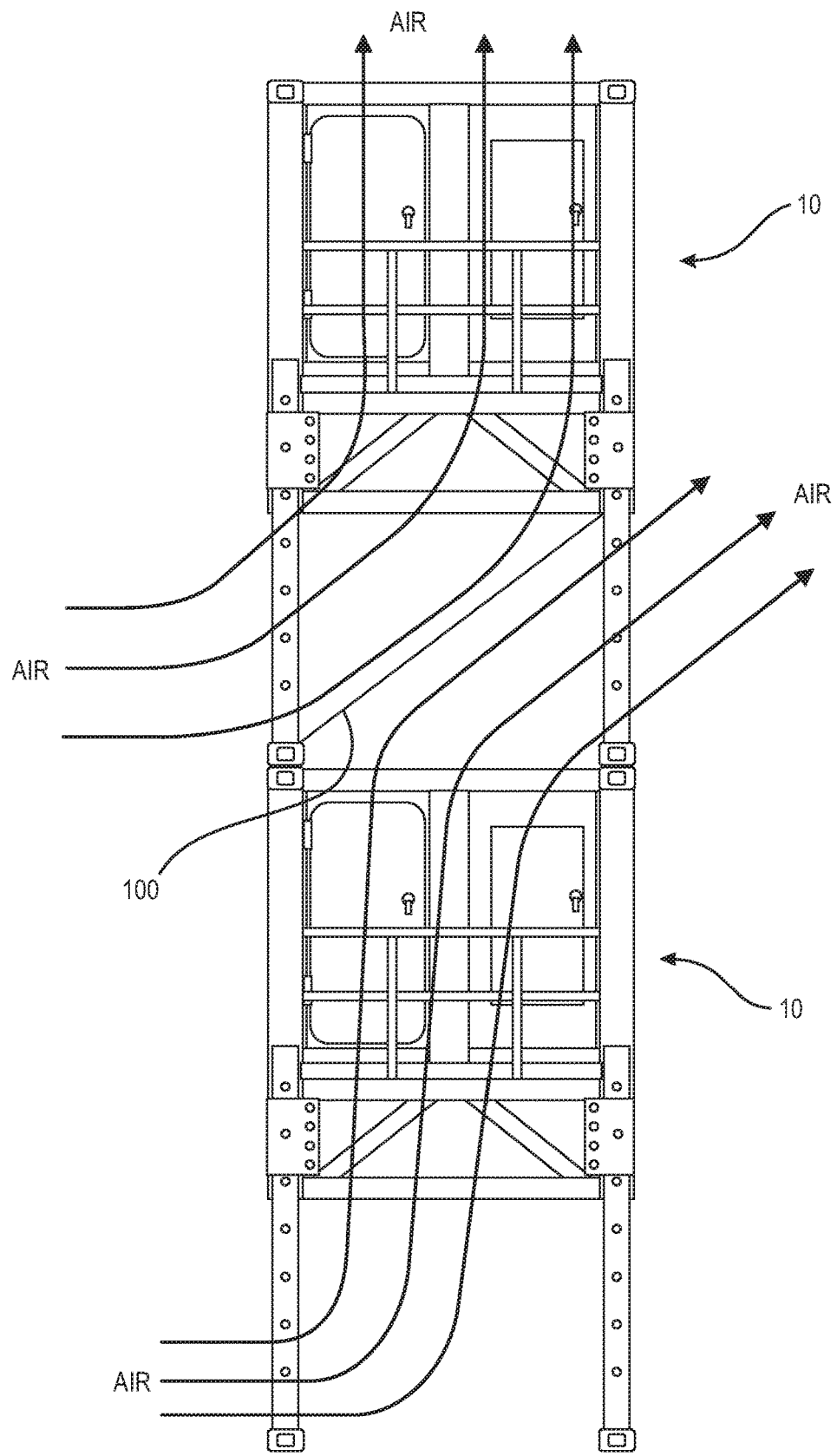
FIG. 18 is an end view of two cooling towers stacked one atop another, also showing an exemplary air flow path.

FIG. 18 is yet another possible placement of cooling towers 10 made possible by the principles of the present invention. This shows two cooling towers 10 placed atop one another. Air flow through each is indicated by the arrowed lines. Note that a partition 100 is preferably positioned below the top cooling tower 10, which diverts hot air exiting the lower cooling tower 10 to one side, and provides for cool air to enter the upper cooling tower 10 from one side. The ability to stack cooling towers 10 is of value in settings where a relatively tall but narrow space is available.

Figure 19:
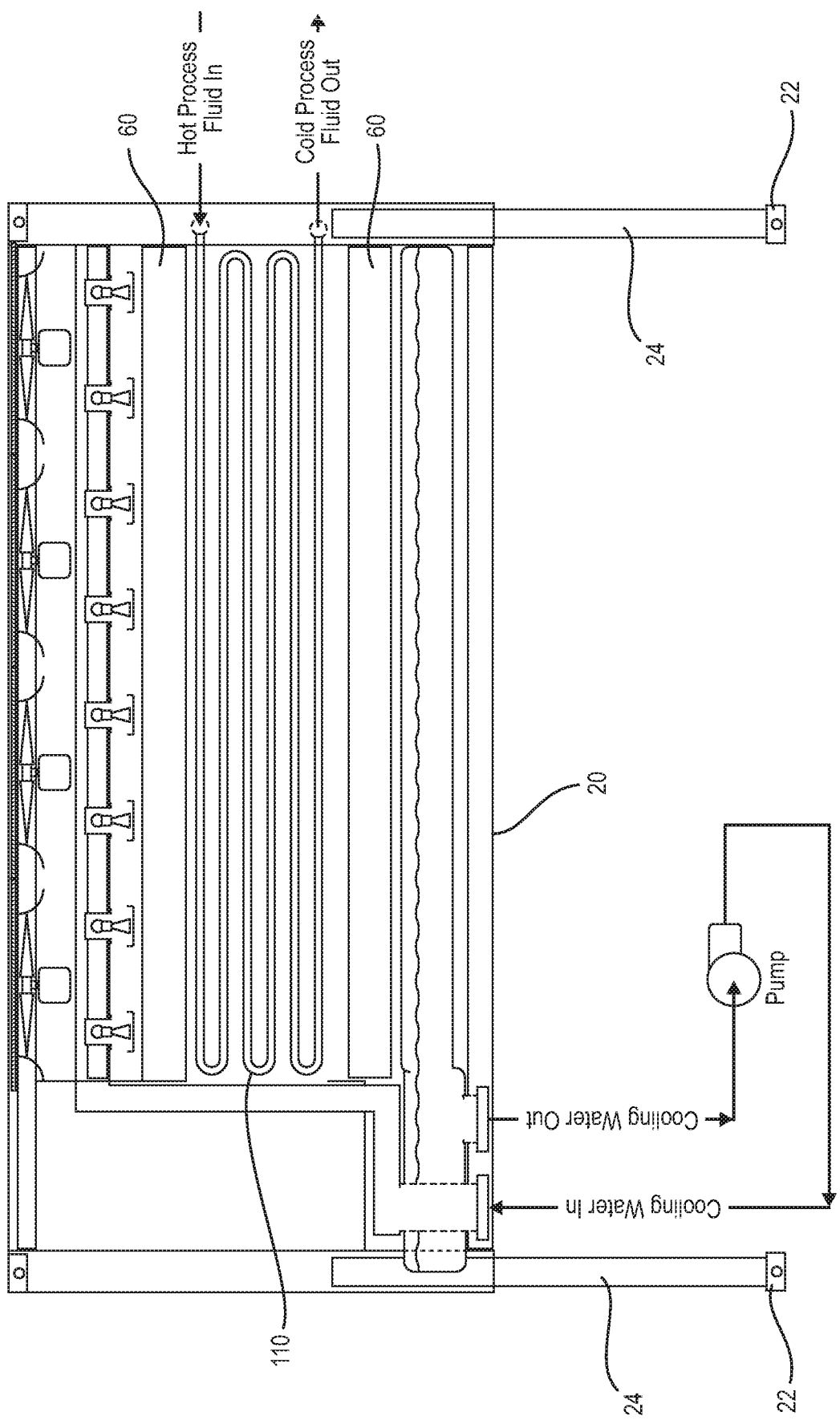
FIG. 19 is a side view in partial cross section of a cooling tower embodiment comprising cooling tubes routed through the cooling tower, for cooling of fluids flowing through the tubes.

FIG. 19 illustrates yet another embodiment of the cooling tower 10 embodying the principles of the present invention. In this embodiment, the objective of the system is to cool fluids flowing through coils 110, while at the same time (if desired) cooling hot water to be sprayed onto a fill media 60 and/or coils 110. Coils 110 are placed in the central portion of cooling tower 10, where fill media 60 would normally be, and are thus exposed to cold water cascading downwardly from above; it is understood that water is pumped through the system generally as described in connection with the preceding embodiments. Heat is therefore transferred from the fluids flowing through coils 110, to the coil 110 surface, then to the cold water flowing onto/by the coils, thereby cooling the fluids flowing through coils 110. It is understood that coils 110 may effectively be embedded within fill media 60.

FIGS. 20 and 21 show a water flow control arrangement, to control water flow individually to each lateral 83 from header 82. A tubular section 200 is disposed through header 82, spanning the width of header 82. Tubular section 200 comprises a hole 210 through the wall thereof, through which water can flow from header 82. Tubular section 200 is fluidly connected to laterals 83. Tubular section 200 is rotatably mounted, with respect to both header 82 and laterals 83 (that is, tubular section 200 can be rotated without rotation of header 82 and laterals 83). Seals 202 provide a fluid seal between tubular section 200 and header 82, and between tubular section 200 and laterals 82. By rotation of tubular section 200, water flow rate from header 82 into laterals 83 can be adjusted for each lateral 83, thereby permitting balancing of water flow rate through each lateral 83 (so as to equalize flow in each lateral).

It is understood that pumps, controls, valves, digital processors (i.e. computers), electrical components, gauges, and other components, as generally known in the relevant art, are also part of cooling tower 10.

CONCLUSION

While the preceding description contains many specificities, it is to be understood that same are presented only to describe some of the presently preferred embodiments of the invention, and not by way of limitation. Changes can be made to various aspects of the invention, without departing from the scope thereof.

Therefore, the scope of the invention is to be determined not by the illustrative examples set forth above, but by the appended claims and their legal equivalents.

We claim:

1. An evaporative cooling tower for the cooling of water, comprising:
   a single frame forming an ISO (International Organization for Standardization) compliant shipping container, having a length, a width, a height, and four upper and four lower corners, and comprising ISO compliant shipping container corner fittings at each of said upper corners and said lower corners, wherein said ISO compliant shipping container corner fittings are used to secure the ISO compliant shipping container; and
   a single cooling tower main body having a length, a width, a height, and positioned within said single frame as a length direction of said single cooling tower main body matches a length direction of said single frame,
      wherein said single cooling tower main body comprises:
      a fill media, for passage of water downward therethrough;
      a means for moving air vertically upward through said fill media;
      a means for distributing water across an upper surface of said fill media; and
      a water collection system positioned below said fill media, wherein said water collection system comprises air flow paths therethrough and configured such that air may enter said evaporative cooling tower from its bottom surface and pass upwardly through said water collection system, thereby permitting placement of multiple units adjacent one another while retaining adequate air flow, while water flowing downwardly out of said fill media is collected by said water collection system, wherein said water collection system comprises a plurality of troughs arranged in a single layer, wherein said plurality of troughs are configured so that: a length direction dimension of each of said plurality of troughs spans substantially a length direction of said fill media; a width direction of each of said plurality of troughs matches a width direction of said single cooling tower main body; and said plurality of troughs are spaced from each other in the width direction of said single cooling tower main body, wherein each of said plurality of troughs comprises a first upper edge and a second upper edge, wherein said upper first edge is provided with a baffle extending from said first upper edge toward said fill media and angled with respect to a bottom surface of said fill media to allow water flowing downwardly out of said fill media to flow into said plurality of troughs, wherein said second upper edge is provided with an air flow space above said second upper edge and forming a part of said air flow paths, wherein the baffles of a part of troughs of said plurality of troughs located at one end in the width direction of the single cooling tower main body and the baffles of other part of troughs of said plurality of troughs located at another end in the width direction of the single cooling tower main body are provided so that: an angle is formed as the baffles of said part of troughs are inclined toward said another end as well as the baffles of said other part of troughs are inclined toward said one end with respect to a vertical direction of the single cooling tower main body.

2. The evaporative cooling tower of claim 1, wherein said water collection system comprises a trough unit, wherein said trough unit comprises said plurality of troughs and a central trough, wherein said plurality of troughs and a central trough are separated from each other in the width direction of the single cooling tower body and arranged in a single layer, wherein said central trough is located at center of the width direction of said single cooling tower main body, said part of troughs of said plurality of troughs are located between said central trough and said one end in the width direction of said single cooling tower main body, and said other part of troughs of said plurality of troughs are located between said central trough and said other end in the width direction of said single cooling tower main body, wherein said central trough is configured so that: a length direction dimension of said central trough spans substantially a length direction of said fill media; a width direction of said central trough matches a width direction of said single cooling tower main body, wherein said central trough comprise two upper edges, wherein said each of two upper edges is provided with an air flow space above and forming a part of said air flow paths, wherein said trough unit is configured so that: water flowing downwardly out of said fill media and then flowing into said plurality of troughs and said central trough may continue flow along length directions of said plurality of troughs and said central trough, as well as air may flow vertically upward through spaces between said plurality of troughs and said central trough, and through said air flow space above at least one of said plurality of troughs and said central trough.

3. The evaporative cooling tower of claim 2, further comprising louvers disposed in said air flow spaces.

4. The evaporative cooling tower of claim 2, wherein said means for moving air vertically upward through said fill media comprises one or more fans positioned above said fill media.

5. The evaporative cooling tower of claim 4, further comprising a drift eliminator positioned above said fill media, and wherein said means for distributing water across an upper surface of said fill media comprises a plurality of nozzles for water distribution having no moving parts, positioned between said upper surface of said fill media and a lower surface of said drift eliminator, said plurality of nozzles positioned within a range of about 0.25" to 1.0" above said upper surface of said fill media, and wherein a distance between said upper surface of said fill media and said lower surface of said drift eliminator is less than 10 inches.

6. The cooling evaporative tower of claim 5, wherein water flowing into said troughs and flowing along the length direction of said troughs flows from said plurality of troughs into a basin disposed at one end of each of said plurality of troughs and positioned within said ISO compliant shipping container, said water flowing into said basin without changing its direction of flow, and wherein said plurality of troughs and said basin form an integral unit.

7. The evaporative cooling tower of claim 6, further comprising a piping and pump system, disposed within said ISO compliant shipping container, which receives water from said basin and pumps same to a system to be cooled.

8. The evaporative cooling tower of claim 7, further comprising vertically disposed telescoping legs positioned at each corner of said single frame, wherein a lower end of each of said legs comprises an ISO compliant shipping container corner fitting, and wherein each of said legs are telescoped to and fixed at a desired length extended from said ISO compliant container.

9. The evaporative cooling tower of claim 1, further comprising vertically disposed telescoping legs positioned at each corner of said single frame, wherein a lower end of each of said legs comprises an ISO compliant container corner fitting, and wherein each of said legs are telescoped to and fixed at a desired length extended from said ISO compliant container.

10. The evaporative cooling tower of claim 2, further comprising vertically disposed telescoping legs positioned at each corner of said single frame, wherein a lower end of each of said legs comprises an ISO compliant container corner fitting, and wherein each of said legs may be telescoped to and fixed at a desired length extended from said ISO compliant container.

11. The evaporative cooling tower of claim 4, further comprising vertically disposed telescoping legs positioned at each corner of said single frame, wherein a lower end of each of said legs comprises an ISO compliant container corner fitting, and wherein each of said legs may be telescoped to and fixed at a desired length extended from said ISO compliant container, thereby positioning said cooling tower at a desired height for proper drainage of said water.

12. The evaporative cooling tower of claim 8, wherein said fill media is supported by a grating which spans substantially the length and width of said fill media.

13. The evaporative cooling tower of claim 12, wherein a velocity of water flowing the length of said plurality of troughs is sufficient to minimize sediment accumulation within said troughs.

* * * * *